(12) United States Patent
Weinstein et al.

(10) Patent No.: US 7,429,611 B2
(45) Date of Patent: Sep. 30, 2008

(54) INDOLE INHIBITORS OF 15-LIPOXYGENASE

(75) Inventors: David S. Weinstein, East Windsor, NJ (US); Charles M. Langevine, Brooklyn, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 236 days.

(21) Appl. No.: 11/232,063

(22) Filed: Sep. 21, 2005

(65) Prior Publication Data

US 2006/0063822 A1    Mar. 23, 2006

Related U.S. Application Data

(60) Provisional application No. 60/612,463, filed on Sep. 23, 2004.

(51) Int. Cl.
*A61K 31/405* (2006.01)
*C07D 403/02* (2006.01)

(52) U.S. Cl. .................. 514/414; 514/419; 548/465; 548/492

(58) Field of Classification Search ............... 548/492, 548/465; 514/414, 419
See application file for complete search history.

(56) References Cited

U.S. PATENT DOCUMENTS

| | | | |
|---|---|---|---|
| 5,612,359 | A | 3/1997 | Murugesan |
| 5,712,279 | A | 1/1998 | Biller et al. |
| 5,739,135 | A | 4/1998 | Biller et al. |
| 5,760,246 | A | 6/1998 | Biller et al. |
| 6,043,265 | A | 3/2000 | Murugesan et al. |
| 6,548,529 | B1 | 4/2003 | Robl et al. |
| 6,706,720 | B2 | 3/2004 | Atwal et al. |

FOREIGN PATENT DOCUMENTS

WO    WO 00/01389    1/2000

OTHER PUBLICATIONS

Misztal et al. "New Synthesis of 5-Nitro- and 5-Benzyloxytryptamine and their N-acylderivatives" Polish Journal of Pharmacology and Pharmacy, 1984, vol. 36, Iss 4, pp. 345-349.*
Bleich, D. et al., "Resistance to type 1 diabetes induction in 12-lipoxygenase knockout mice", The Journal of Clinical Investigation, vol. 103, No. 10, pp. 1431-1436 (1999).
Bocan, T. et al., "A specific 15-lipoxygenase inhibitor limits the progression and monocyte-macrophage enrichment of hypercholesterolemia-induced atherosclerosis in the rabbit", Atherosclerosis, vol. 136, pp. 203-216 (1998).
Chu, L. et al., "Synthesis of 2-aryltryptamines with Palladium Catalyzed Cross-Coupling of 2-Bromotryptamines and Arylboronic Acids", Tetrahedron Letters, vol. 38, No. 22, pp. 3871-3874 (1997).
Ducry, L. et al., "Synthesis of 1,2,5-Thiadiazolidin-3-one 1,1-Dioxide Derivatives and Evaluation of Their affinity for MHC Class-II Proteins", Helvetica Chimica Acta, vol. 82, pp. 2432-2447 (1999).
Gan, Qing-Fen et al., "Defining the Arachidonic Acid Binding Site of Human 15-Lioxygenase", The Journal of Biological Chemistry, vol. 271, No. 41, pp. 25412-25418 (1996).
Jiang, Zhen-Yue et al., "Lipid Hydroperoxide Measurement by Oxidation in $Fe^{2+}$ in the Presence of Xylenol Orange. Comparison with the TBA Assay and an Iodometric Method", Lipids, vol. 26, No. 10, pp. 853-856 (1991).
Kelavkar, U. et al., "The Effect of 15-Lipoxygenase-1 Expression on Cancer Cells", Current Urology Reports, vol. 3, pp. 207-214 (2002).
Rapoport, S. et al., "The Lipoxygenase of Reticulocytes", Eur. J. Biochem., vol. 96, pp. 545-561 (1979).
Setty, B.N. et al., "15-Hydroxyeicosatetraenoic Acid-Mediated Potentiation of Thrombin-Induced Platelet Functions Occurs Via Enhanced Production of Phosphoinositide-Derived Second Messengers—sn-1,2-Diacylglycerol and linositol-1,4,5-Trisphosphate", Blood, vol. 80, No. 11, pp. 2765-2773 (1992).
Soti, F. et al., "Preparation of 7-Methoxyryptamine", Synthetic Communications, vol. 23, No. 12, pp. 1689-1698 (1993).
Sultana, C. et al., "Lipoxygenase Metabolites Induced Expression of Adhesion Molecules and Transendothelial Migration of Monocyte-Like HL-60 cells is Linked to Protein Kinase C Activation", Journal of Cellular Physiology, vol. 167, pp. 477-487 (1996).
Takechi, H. et al., Intramolecular Photoreactions of Phthalimide-Alkene systems. Oxetane Formation of N-(ω-Indol-3-ylalkyl)phthalimides[1] [Chem.] Pharm. Bull., vol. 36, No. 8, pp. 2853-2863 (1988).
Tisdale, Michael J., "Protein Loss in Cancer Cachexia" Science, vol. 289, pp. 2293-2294 (2000).
Weinstein, David et al., "Tryptamine and homotryptamine-based sulfonamides as potent and selective inhibitors of 15-lipoxygenase", Bioorganic & Medicinal Chemistry Letters, vol. 15, pp. 1435-1440 (2005).

* cited by examiner

*Primary Examiner*—Rei-tsang Shiao
*Assistant Examiner*—Joseph R Kosack
(74) *Attorney, Agent, or Firm*—Hong Liu; Maureen S. Gibbons

(57) ABSTRACT

The present invention provides indole inhibitors of 15-LO, pharmaceutical compositions containing such inhibitors and methods for treating diseases related to the 15-LO cascade using such compounds and compositions.

4 Claims, No Drawings

INDOLE INHIBITORS OF 15-LIPOXYGENASE

RELATED APPLICATIONS

This application claims priority benefit under Title 35 § 119(e) of U.S. Provisional Application No. 60/612,463, filed Sep. 23, 2004, the contents of which are herein incorporated by reference

FIELD OF THE INVENTION

The present invention relates to indole inhibitors of the enzyme 15-lipoxygenase ("15-LO"), pharmaceutical compositions comprising said inhibitors, and methods of treating diseases responsive to inhibition of 15-lipoxygenase.

BACKGROUND OF THE INVENTION

The 15-LO cascade is implicated in various inflammatory disorders, including disorders involving the origin and recruitment of foam cells. Cholesterol is transported in blood particles called lipoproteins, which include low-density lipoproteins (LDL). Lipoproteins contain cholesterol and are necessary for foam cell formation. The formation of foam cells can lead to serious disorders. For example, hypercholesterolemia can induce monocytes to migrate into the arterial wall and mature into foam cells or tissue macrophages that accumulate fatty material, including cholesterol esters. Continued creation of foam cells thickens the inner lining of medium and large arteries, thereby forming atherosclerotic plaques or lesions containing cholesterol, smooth muscle cells, and connective tissue cells. Affected arteries lose elasticity and become narrowed or obstructed by the plaques indicating the onset of atherosclerosis. Atherosclerotic plaques may collect calcium, become brittle, and even rupture triggering the formation of a blood clot or thrombus capable of occluding an artery and causing a stroke or heart attack. In addition to atherosclerosis, hypercholesteremia plays a role in peripheral vascular diseases of small arteries, veins and lymphatics. Thus, hypercholesteremia may also affect the arms, legs, kidneys and other vital organs in addition to the heart and brain.

Lipoxygenases are enzymes that catalyze the oxidation of polyunsaturated fatty acids and esters thereof, including those found in low-density lipoproteins. In addition to metabolism of free fatty acids, the enzyme 15-lipoxygenase (15-LO) also oxidizes esterified polyenoic fatty acids. Related to its general pathology, it is believed that oxidative metabolites of the 15-LO cascade [e.g. the arachidonic acid metabolite 15-hydroperoxyeicosatetraenoic acid (15-HPETE)], induce endothelial cell activation and subsequent adhesion molecule expression resulting in monocyte recruitment to the vessel wall [Sultana et al, J. of Cellular Physiology 167 (1996) 467-487]. 15-Hydroxyeicosatetraenoic acid (15-HETE), a reduction product of 15-HPETE, has also been implicated in the potentiation of thrombin-induced platelet activation [Setty et al, Blood, 80:11 (1992): 2765-2773]. It has also been demonstrated that arachidonic acid metabolites of the 15-LO cascade, namely 15-hydroperoxyeicosatetraenoic acid (15-HPETE), induce a pro-thrombotic state in endothelial cells through enhancement of plasminogen activator inhibitor-1 (PAI-1) release. Additionally, evidence that 15-LO is involved in the pathology of diabetes, it has been demonstrated that deletion of the mouse gene homologue of 15-LO leads to a reduction of disease progression [Bleich et al, J Clin Invest (1999) May 15;103(10):1431-6]. 15-LO has also been implicated in the progression of various cancers [Kelavkar et al, Curr Urol Rep 2002 Jun.; 3(3):207-14]. Not only in the progression of the cancer itself, but also in its related pathologies including cachexia and wasting [Tisdale et al, Science 2000 Sep. 29;289(5488):2293-4].

Inhibition of 15-LO, therefore, would be useful to prevent and treat diseases with either an inflammatory component, a thrombotic component, or both as in the case of atherosclerosis, as well as various cancers. For example, it has been shown that treatment with a 15-LO inhibitor suppressed atherogenesis (or the production of atheroma—a fatty degeneration of the arterial wall) in rabbits fed a high-fat diet [Bocan et al, Atherosclerosis, 136 (1998): 203-216]. Additional diseases in which treatment with a 15-LO inhibitor would be useful include asthma, psoriasis, osteoarthritis, rheumatoid arthritis, Alzheimer's disease, and chronic obstructive pulmonary disease.

SUMMARY OF THE INVENTION

The present invention provides indole inhibitors of 15-LO, pharmaceutical compositions containing such inhibitors, and methods for treating diseases related to the 15-LO cascade using such compounds and compositions. Specifically, the invention provides compounds of Formula I:

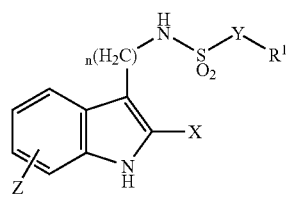

including enantiomers, diastereomers, salts and solvates thereof wherein:

Z is hydrogen;

X is selected from the group consisting of —C(O)NR$^2$R$^3$, —C(O)OH, aryl heteroaryl and —C(O)—, wherein the —C(O)— is bonded to the nitrogen of the sulfonylamino group to form a six- or seven membered lactam, wherein each aryl and heteroaryl may optionally br substituted with one or more substituents Selected from the froup consisting of halo, alkyl, perfinoroalkyl, alkoxy, amino, carboxylic acid, Ester and amide;

Y is selected from the group consisting of a direct bond, aryl, heteroaryl, amido, amino, hydroxyl, alkoxy, halo,

carboxylic acid, alkylester and

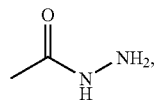

wherein each alkyl, aryl, heteroaryl, amido and amino may optionally be substituted with one Or more substituents selected from the group consisting of alkyl, cycloalkyl, aryl, heteroaryl, amido, amino, hydroxyl, alkoxy and halo;

$R^2$ and $R^3$ are independently selected from ther group consisting of H, alkyl, cycloalkyl, Heterocyclyl, aryl and heteroaryl; and n is 2 and 3.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are often most preferred.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like.

The term "perfluoroalkyl" as used herein by itself or as part of another group refers to an alkyl group wherein the hydrogen atoms have been replaced by fluorine atoms.

The term "alkoxy" as used herein by itself or as part of another group refers to an alkyl, alkenyl or alkynyl group attached as a substituent through an ether, —O—, linkage.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

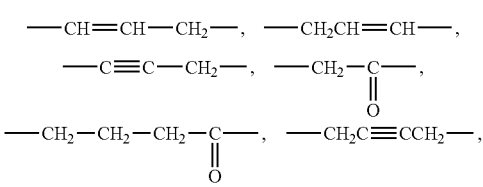

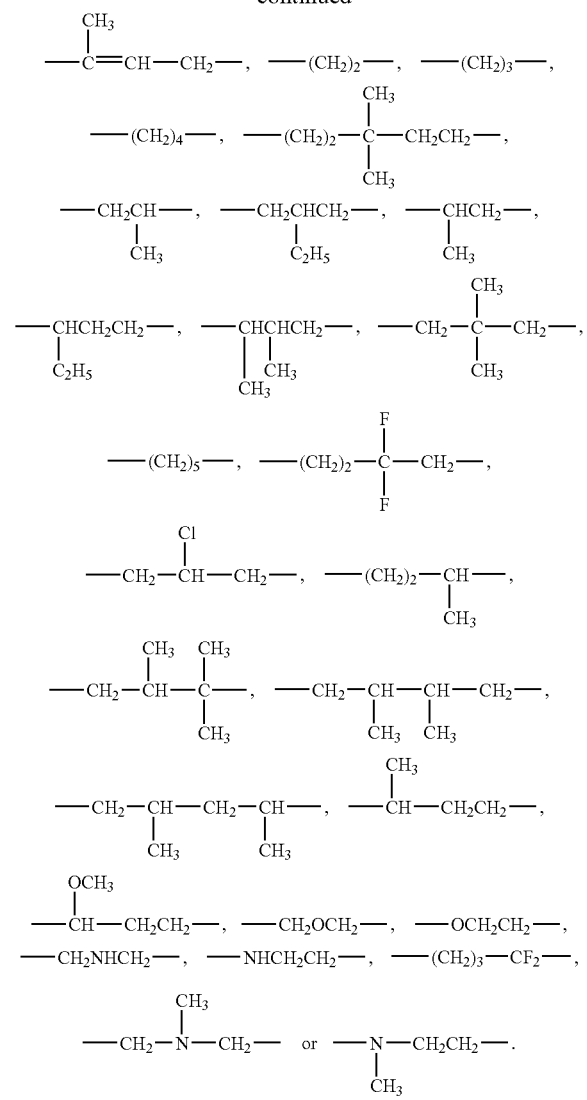

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The rings of multi-ring cycloalkyls may be either fused, bridged and/or joined through one or more spiro union to 1 or 2 aromatic cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

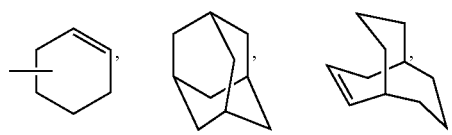

-continued

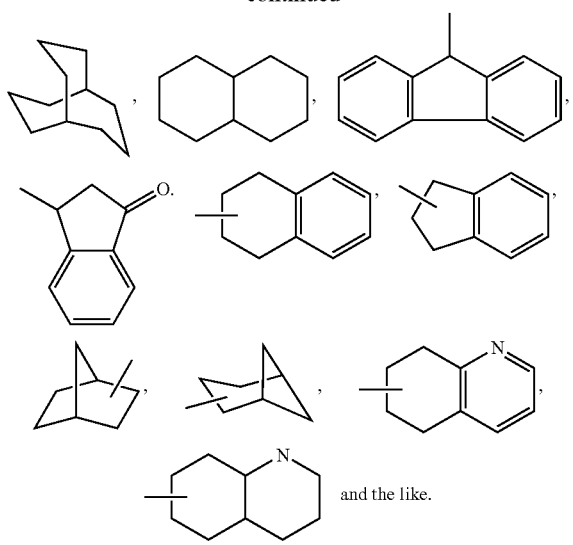

and the like.

The term "cycloalkylene" as employed herein refers to a "cycloalkyl" group which includes free bonds and thus is a linking group such as

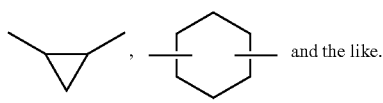 and the like.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

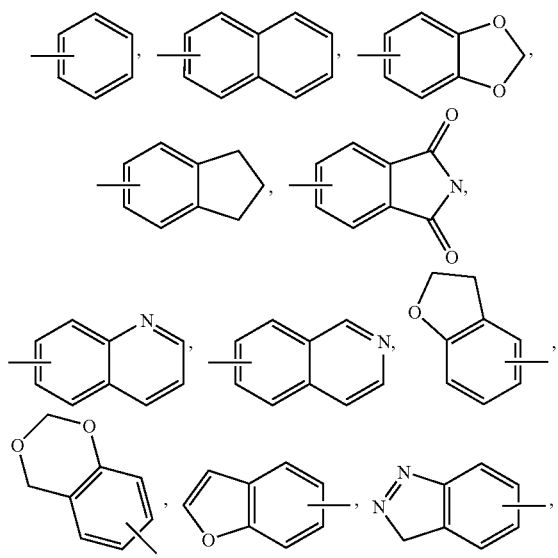

-continued

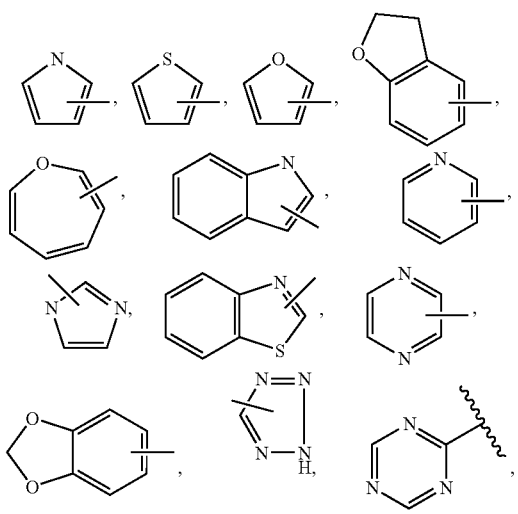

and the like.

The terms "halogen" and "halo" as used herein by itself or as part of another group refer to fluorine, chlorine, bromine and iodine. Haloalkyl refers to an alkyl chain substituted with from one to three halogens.

The term "heteroaryl" as used herein by itself or as part of another group refers to monocyclic, bicyclic and tricyclic aromatic rings containing from 5 to 113 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include the following:

-continued

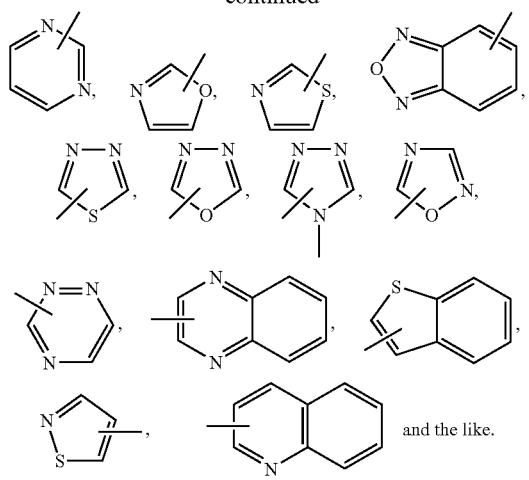

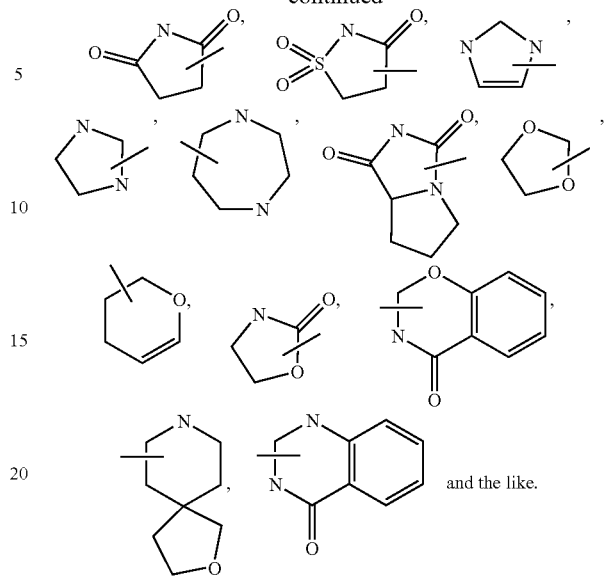

and the like.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a hetero atom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

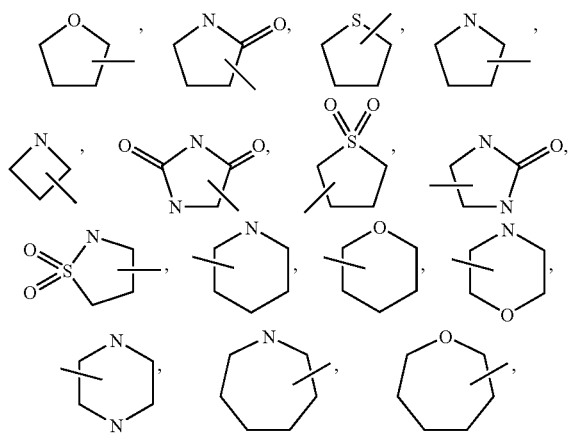

The term "carboxylic acid" as used herein by itself or as part of another group refers to the group —C(O)OH.

The term "ester" as used herein by itself or as part of another group refers to the groups —C(O)O— and —O(O)C—, wherein the groups are further substituted with groups such as, for example, alkyl, alkenyl, alkynyl, perfluoroalyl, cycloalkyl, heterocyclic, aryl, heteroaryl.

The term "amide" as used herein by itself or as part of another group refers to the groups

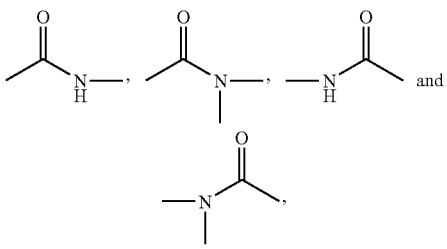

wherein the groups are further substituted with groups such as, for example, alkyl, alkenyl, alkynyl, perfluoroalyl, cycloalkyl, heterocyclic, aryl, heteroaryl.

The term "amine" as used herein by itself or as part of another group refers to the groups

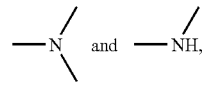

wherein the groups are further substituted with groups such as, for example, alkyl, alkenyl, alkynyl, perfluoroalyl, cycloalkyl, heterocyclic, aryl, heteroaryl.

The above-defined groups may optionally have one or more hydrogen atoms that are attached to a carbon atom substituted with any group known to one of skill in the art.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl), and each of which (homocyclic or heterocyclic) may optionally be substituted by one or more (such as one to three) hydrogen, halogen, cyano, alkyl, alkoxy, nitro or trifluoromethyl groups.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates. Any tautomers which may exist are also contemplated herein as part of the present invention.

All stereoisomers of the present compounds, such as those which may exist due to asymmetric carbons on the R substituents, including enantiomeric forms (which may exist even in the absence of asymmetric carbons, e.g., atropisomers) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

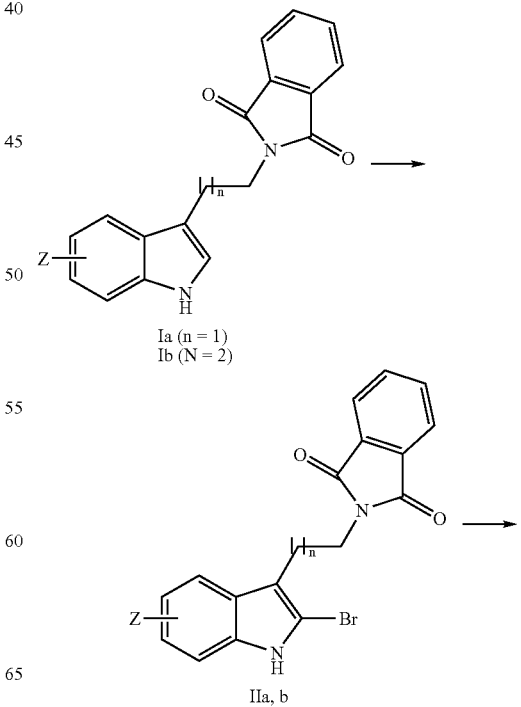

SCHEME I
Synthesis of C-2 substituted tryptamine and homotryptamine derivatives

-continued

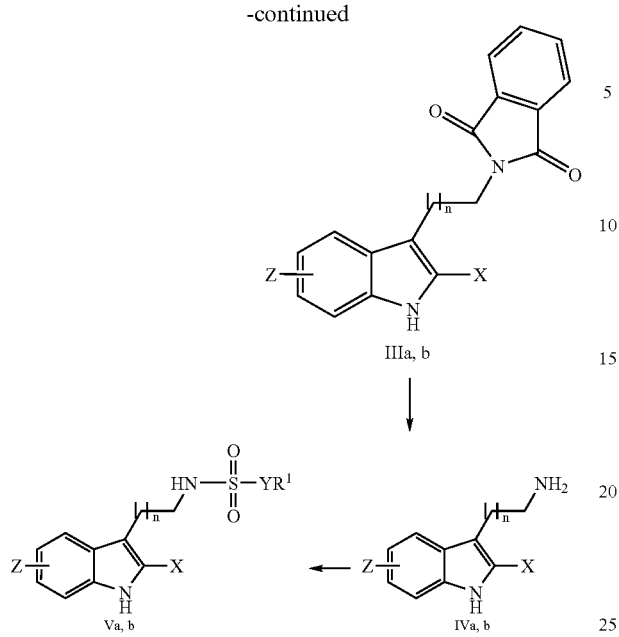
IIIa, b

↓

Va, b    ←    IVa, b

Scheme I illustrates a general method for the synthesis of C-2 aryl substituted trypamine or homotryptamine derivatives. The procedures closely follow those described in the literature by Chu et al. [(*Tetrahedron Lett.*, 38(22) 3871-3874 (1997)]. Thus, phthalimide-protected tryptamine (Ia) or homotryptamine (Ib, prepared from homotryptamine; see Takechi, H.; Machida, M.; Kanaoka, Y. *Chem. Pharm. Bull.* 1988, 36, 2853) may be regioselectively brominated at C-2 by treatment with an appropriate brominating reagent (ideally pyridinium tribromide). Suzuki coupling with a suitable boronic acid [$XB(OH)_2$] or boronate ester (such as pinacol boronate $XB[OC(CH_3)_2]_2$) under standard conditions [catalytic Pd(0), 2M aqueous sodium carbonate, toluene/ethanol] provides the C-2 functionalized phthalimido tryptamine (IIIa) and homotryptamine IIIb. Subsequent removal of the phthalimide group under standard conditions (hydrazine in warm methanol or THF/methanol mixture) gives the corresponding amines (IVa,b). Sulfonamide derivatives of the amine may be readily prepared by treatment with sulfonyl chlorides in the presence of tertiary amine (triethylamine or diisopropylethyl amine) in dichloromethane. Sulfamide derivatives of the amines IVa,b may be prepared by treatment with a sulfamoyl chloride in the presence of tertiary amine base. Non-symmetrical sulfamides may be prepared via intermediate N-sulfamoyloxazolidinones following the method of Ducry et al. (Helv. Chim. Act. 1992, 82 (12), 2432-2447). Typically, to 1 eq. of chlorosulfonyl isocyanate in dry dichloromethane (0.22 M) at −20° C. is added 2-chloroethanol dropwise. The temperature is allowed to warm to 0° C. and the solution maintained at that temperature for 1.5 h. The solution is then cooled to −20° C. and added via canula to a solution (or suspension) of an amine (1 eq.) and triethylamine (7 eq) in dichloromethane (0.25 M) at 0° C. The reaction mixture is allowed to warm to and maintained at room temperature 16 h. The intermediate sulfamoyloxazolidinone may be purified by preparative HPLC. Alternatively, the reaction mixture may be concentrated in vacuo and used directly in the next step without further purification.

Heating a solution of the intermediate sulfamoyloxazolidinone in dry acetonitrile (0.1-0.5 M) in the presence of a second amine and excess triethylamine (7-10 eq) at 70° C. for 17 h, followed by purification by preparative HPLC provides the sulfamides.

SCHEME II
Synthesis of C-2 carboxy- substituted tryptamine derivatives

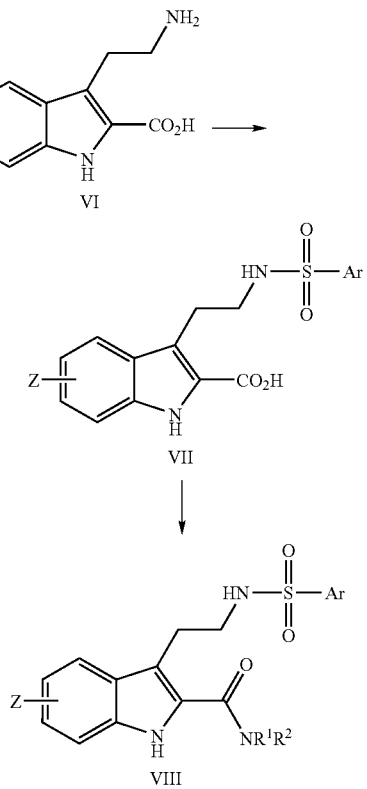

Scheme II illustrates the preparation of C-2 carboxy-sustituted tryptamine derivatives. Tryptamine 2-carboxylic acid (VI) may be prepared following the method of Soti, et al. *Synth. Comm.* 1993, 23(12)1689. Treatment of VI with an arylsulfonyl chloride in the presence of an appropriate base (typically sodium carbonate in water) may provide carboxylic acid VII. The carboxylic acid functionality may be further elaborated to carboxamides (VIII) by treatment with amine in the presence of an appropriate reagent mixture for activation of the carboxylic acid (typically HOBT and EDC).

Utility and Combinations

The compounds of formula I and salts thereof are inhibitors of 15-LO and are useful in treatment of various inflammatory disorders, including disorders involving the origin and recruitment of foam cells. The compounds of the present invention may be employed alone or in combination with each other and/or other suitable therapeutic agents useful in the treatment of 15-LO mediated disorders such as atherosclerosis, treating or preventing inflammation; diabetes; vascular restenosis; hypertension; asthma; rheumatiod arthritis; osteoarthritis; cancer; and inflammatory bowel disease.

Additionally, the compounds are useful in treating or preventing symptoms or consequences occurring from thrombosis and/or the formation of atherosclerotic plaques, atherosclerosis, peripheral arterial disease, coagulation syndromes, and intermittent claudication. The compounds may be used to treat thrombotic or thromboembolic conditions such as thromboembolic stroke (including that resulting from atrial fibrillation or from ventricular mural thrombus); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequenses of medication (such as oral contraceptives, hormome replacement and heparin); thrombotic consequenses of atherosclerotic vascular disease and atherosclerotic plaque rupture leading to tissue ischemia; prevention of atherosclerotic plaque formation; transplant atherosclerosis; thromboembolic complications of pregancy including fetal loss; thromboembolic consequenses of thrombophilia (e.g., Factor V Leiden, and homocystinenimia); pro-thrombotic consequenses and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation); coagulation syndromes; vascular remodeling atherosclerosis, restenosis and systemic infection; prevention of metastesis and tumor implantation; diabetic complications including retinopathy, nephropathy and neuropathy; inflammation; Kasabach-Merritt syndrome; atrial fibrillation; ventricular enlargement (including dilated cardiac myopathy and heart failure); restenosis (e.g., following arterial injury-induced either endogenously or exogenously).

In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation. Additionally, the compounds may be used for preservation of tissue as related to organ transplantation.

The inventive compounds also are useful in treating diseases or disorders in other tissues or muscles that are associated with inflammatory conditions. For example, the compounds may be used to treat muscle cell damage and necrosis.

Additionally, the inventive compounds may be useful as anti-cancer and/or anti-tumor agents.

The present invention thus provides methods for the treatment of these disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to endothelin-dependent or angiotensin II-dependent disorders.

The present invention also provides pharmaceutical compositions comprising at least one of the compounds of the formula I capable of treating a 15-LO mediated disorder in an amount effective therefor, and a pharmaceutically acceptable vehicle, carrier or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used.

Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat peripheral vascular diseases and as such may be formulated as a cream or ointment.

The compounds of the present invention may also be employed in combination with other suitable therapeutic agents that a patient suffering from a 15-LO mediated disorder might also likely be taking other therapeutic agents such as potassium channel openers, calcium channel blockers, sodium hydrogen exchanger inhibitors, anti-arrhythmic agents, thrombin inhibitors, platelet aggregation inhibitors or anti-platelet agents, fibrinogen antagonists, diuretics, anti-hypertensive agents, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-oxidant agents; angiogenesis modulators; anti-osteoporosis agents; hormone replacement therapies; oral contraceptives; anti-coagulants; anti-proliferative agents; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

For example, the inventive compounds may be used in combination with aspirin, clopidogrel, ticlopidine or CS-747, warfarin, and low molecular weight heparins (such as lovenox, enoxaparain, and dalteparin). Other suitable therapeutic agents in combination with which the inventive compounds may be used include:

anti-arrhythmic agents including Class I agents (such as propafenone); Class II agents (such as carvedilol and propranolol); Class III agents (such as sotalol, dofetilide, amiodarone, azimilide and ibutilide); Class IV agents (such as ditiazem and verapamil); K+ channel openers such as IAch inhibitors, and IKur inhibitors (e.g., compounds such as those disclosed in U.S. application Ser. No. 09/729,731, filed Dec. 5, 2000;

alpha- or beta-adrenergic blockers (such as propranolol, nadolol and carvedilol), or β-adrenergic agonists such as albuterol, terbutaline, formoterol, salmeterol, bitolterol, pilbuterol, and/or fenoterol;

angiotensin-II receptor antagonists (e.g., irbesartan, losartan or valsartan);

anticholinergics such as ipratropium bromide;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;

anti-depressant or anti-anxiety agents such as nefazodone, sertraline, diazepam, lorazepam, buspirone, and hydroxyzine pamoate;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;

anti-hypertensive agents such as angiotensin-converting enzyme (ACE) inhibitors (e.g., captopril, lisinopril, zofenopril, ramipril, fosinopril, enalapril, ceranopril, cilazopril, delapril, pentopril, quinapril), vasopeptidase inhibitors, i.e., dual ACE/NEP inhibitors (e.g., omapatrilat and gemopatrilat), AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors;

anti-inflammatory agents such as cromolyn, nedocromil, theophylline, zileuton, zafirlukast, monteleukast and/or pranleukast or cortiocosteroids including beclomethasone, triamcinolone, budesonide, fluticasone, flunisolide or dexamethasone; prednisone; dexamethasone; enbrel; protien tyrosine kinase (PTK) inhibitors; cyclooxygenase inhibitors (including NSAIDs, and COX-1 and/or COX-2 inhibitors); aspirin; or indomethacin; other lipoxygenase inhibitors; chemokine receptor modulators (including CCR1, CCR2, CCR3, CXCR2 receptor antagonists); secretory and cytosolic phospholipase A2 inhibitors; VLA4 antagonists; cytokine modulators (e.g. TNF-alpha converting enzyme (TACE) inhibitors, Interleukin-1 converting enzyme (ICE) inhibitors, Interleukin-1 receptor antagonists);

angiogenesis modulators such as endostatin;

anti-oxidant agents and/or lipid peroxidation inhibitors such as probucol, BO-653, Vitamin A, Vitamin E, AGI-1067;

anti-platelet agents such as GPIIb/GPIIIa blockers, (e.g., abciximab, eptifibatide, tirofiban); P2Y12 antagonists (e.g., clopidogrel, ticlopidine, CS-747); or thromboxane receptor antagonists (e.g., ifetroban);

anti-osteoporosis agents including alendronate and raloxifene;

anti-obesity agents including orlistat and aP2 inhibitors (such as those disclosed in U.S. Ser. No. 09/519,079 filed Mar. 6, 2000);

anti-proliferative agents for use in combination with the compounds of the present invention include cyclosporin A, paclitaxel, FK 506, and adriamycin;

anti-ulcer and gastroesophageal reflux disease agents including famotidine, ranitidine, and omeprazole;

sodium hydrogen exchanger-1 (NHE-1) inhibitors such as cariporide;

calcium channel blocking agents such as verapamil, nifedipine, diltiazem, amlodipine and mybefradil;

cardiac glycosides such as digitalis and ouabain;

diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride;

hormone replacement therapies including estrogen (e.g., congugated estrogens) and estradiol;

lipid profile modulators including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, or atavastatin or visastatin)); squalene synthetase inhibitors; fibrates; bile acid sequestrants (such as questran); ACAT1 inhibitors; ACAT2 inhibitors; dual ACAT1/2 inhibitors; MTP inhibitors; cholesterol absorption inhibitors such as Eztemibe; and cholesterol ester transfer protein inhibitors (e.g., CP-529414); PPAR-delta agonists; PPAR-alpha agonists; dual PPAR-alpha/delta agonists; LXR-alpha agonists; LXR-beta agonists; LXR dual alpha/beta agonists;

mineralocorticoid receptor antagonists such as spironolactone and eplirinone;

microsomal triglyceride transport protein inhibitors (such as disclosed in U.S. Pat. Nos. 5,739,135, 5,712,279 and 5,760,246);

phosphodiesterase (PDE) inhibitors including dipyridamole, cilostazol, or sildenafil, or PDE inhibitors in combination with aspirin, ifetroban, picotamide, ketanserin, clopidogrel, and/or thromboxane receptor antagonists or thromboxane A synthetase inhibitors (such as picotamide);

serotonin-2-receptor antagonists (such as ketanserin), fibrinogen receptor antagonists; and thrombolytic agents, such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), factor VIIa inhibitors, factor Xa inhibitors, thrombin inhibitors (such as hirudin and argatroban), animal salivary gland plasminogen activators, PAI-1 inhibitors such as XR-330 and T-686, and inhibitors of $\alpha$-2-antiplasmin such as anti-$\alpha$-2-antiplasmin antibody, prostacyclin mimetics.

The inventive compounds may also be useful in combination with other anticancer strategies and chemotherapies such as taxol and/or cisplatin. The compounds may be used in conjunction with anti-tumor agents such as paclitaxel, adriamycin, epithilones, cisplatin, and carboplatin.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to allow for increased efficacy and/or reduced doses of any of the above agents and therefore minimize potential hemorrhagic side-effects.

If formulated as a fixed dose, such combination products employ the compounds of this invention within the dosage range described and the other pharmaceutically active agent within its effective dosage range. The above other therapeutic agents, when employed in combination with the compounds of the present invention, may be used, for example, in those amounts indicated in the Physicians' Desk Reference (PDR) or as otherwise determined by one of ordinary skill in the art.

The following assays may be employed in ascertaining the degree of activity of a compound as a 15-LO inhibitor. Compounds described in the following Examples have demonstrated measurable activity as 15-LO inhibitors. The inhibitory activity of the Examples against purified 15-LO enzyme was determined using a standard colorimetric assay in which the lipid hydroperoxide product of either linoleic or arachidonic acid [13-hydroperoxyoctadecadienoic acid (13-HPODE) and 15-hydroperoxyeicosatetraenoic acid (15-HPETE), respectively] oxidizes $Fe^{2+}$ under mildly acidic conditions [Jiang et al, Lipids (1991), 26:10, 853-856]. The $Fe^{3+}$ forms a chromophore with xylenol orange that absorbs strongly at 560 nm. Inhibitory activity was compared to an uninhibited (maximal) reaction to yield % inhibition (compound concentration in which enzyme activity is reduced by 50% is termed the IC50). 15-LO enzyme was obtained from phenylhydrazine-treated rabbits and purified according to the method of Rapoport et al [European Journal of Biochemistry (1979) 96:545-561]. In addition to the colorimetric assay, a standard spectrophotometric kinetic assay [Gan et al, J. Biological Chemistry (1996), 271:41; 25412-2541877] was also employed to measure compound activity as 15-LO inhibitors. This assay determines enzyme activity by monitoring the increased absorbance at 234 nm that results from conjugated diene formation of the metabolized substrate. Reactions were carried out 3 minutes and the linear part of the curve was utilized to calculate reaction rates. IC50 calculations were as described for the colorimetric assay.

EXAMPLES

The following Examples illustrate embodiments of the present invention, and are not intended to limit the scope of the claims. Compounds of the Examples are identified by the example and step in which they are prepared (for example, "1A" denotes the title compound of step A of Example 1), or by the example only where the compound is the title compound of the example (for example, "4" denotes the title compound of Example 4).

General Procedure:

Purification by Reverse-Phase Preparative HPLC

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol/water mixtures in the presence of 0.1% trifluoroacetic acid ("TFA").

Analytical HPLC Methods Employed in Characterization of Examples

Analytical HPLC was performed on Shimadzu LC10AS liquid chromatographs using either of the following methods:

Method A:
Linear gradient of 0 to 100% solvent B over 4 minutes ("min"), with 1 min hold at 100% B.
Ultraviolet ("UV") visualization at 220 nanometers ("nm")
Column: YMC S5 ODS Ballistic 4.6×50 mm
Flow rate: 4 milliliters ("ml")/min
Solvent A: 0.2% phosphoric acid, 90% water, 10% methanol ("MeOH")
Solvent B: 0.2% phosphoric acid, 90% methanol, 10% water Method B:
Linear gradient of 0 to 100% solvent B over 2 min, with 1 min hold at 100% B.
UV visualization at 220 nm
Column: Phenomenex 4.6×30 mm
Flow rate: 5 ml/min
Solvent A: 0.1% trifluoroacetic acid, 90% water, 10% methanol
Solvent B: 0.1% trifluoroacetic acid, 90% methanol, 10% water

Example 1

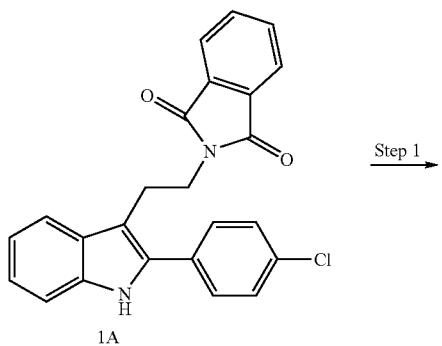

1A

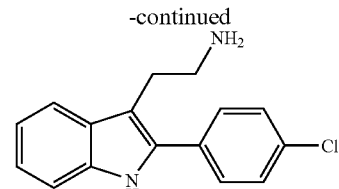

1B

Step 2

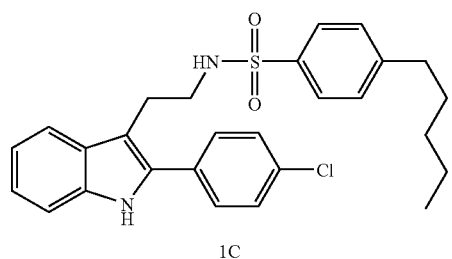

1C

Step 1:

A solution of the phthalimide 1A [prepared according to the literature report: Chu, L. et al., Tetrahetron Lett., 38(22) 3871-3874 (1997)] (18 mg, 0.045 mmol) in methanol (1.5 mL) and THF (0.5 mL) was treated with hydrazine monohydrate (0.05 mL) and heated at 75° C. for 1 h. After cooling and filtration through a syringe-tip filter (0.45 micron, PTFE), the mixture was purified by reverse phase HPLC to provide the product (0.016 g, 95% yield) as a solid, mono trifluoroacetic acid salt. Mass Spectrometry ("MS") (E+) m/z: 271 (MH$^+$); LC retention time (Method A): 2.36 min.

Step 2:

To a solution of the amine 1B (16 mg, 0.042 mmol) in dichloromethane (1 mL) at 0° C. was added triethylamine (0.018 mL, 0.126 mmol) and 4-pentylbenzene-1-sulfonyl chloride (13 mg, 0.054 mmol). The reaction mixture was partitioned between ethyl acetate (10 mL) and 1N aqueous HCl (10 mL). The organic layer was washed with saturated aqueous sodium bicarbonate (10 mL) and brine (10 mL), dried over sodium sulfate, and concentrated. Purification of the residue by preparative TLC (0.5 mm silica, 20 cm×20 cm, 30% ethyl acetate in hexanes as eluent) provided the title compound (1C) as a solid (11.72 mg, 61% yield). MS (E+) m/z: 481 (MH$^+$); LC retention time (Method A): 4.28 min.

Examples 2 to 26

The following Examples 2 to 26 were prepared according to analogous procedures as used to prepare 1C from 1A via 1B as described according to the literature report [Chu, L. et al., Tetrahedron Lett., 38(22) 3871-3874 (1997)] and the methods described above.

| Ex. # | Structure | RT (min.) | HPLC Method | M/z (MH)+ |
|---|---|---|---|---|
| 2 | | 4.12 | A | 477 |
| 3 | 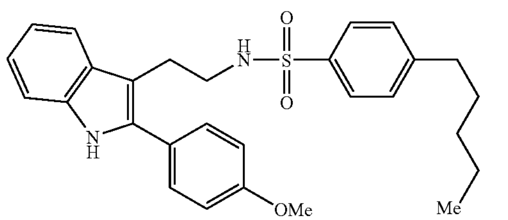 | 3.88 | A | 483 |
| 2 | | 4.12 | A | 447 |
| 5 | 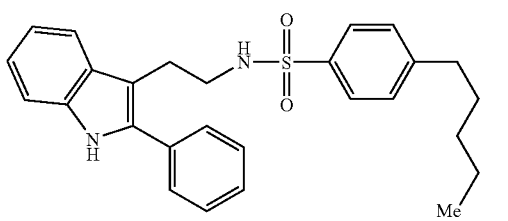 | 4.23 | A | 461 |
| 6 | 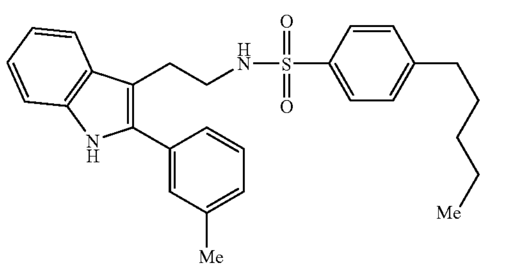 | 3.36 | A | 547 |
| 7 | 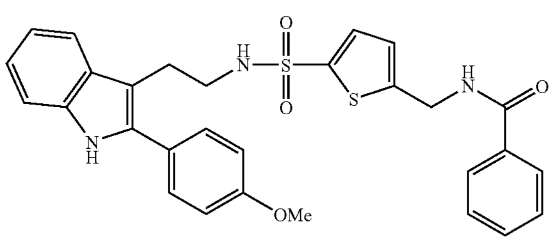 | 2.83 | A | 411 |

-continued

| Ex. # | Structure | RT (min.) | HPLC Method | M/z (MH)+ |
|---|---|---|---|---|
| 8 | 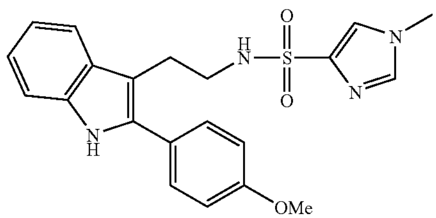 | 4.28 | A | 487 |
| 9 | 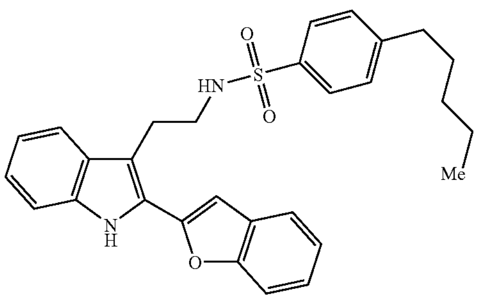 | 3.67 | A | 486 |
| 10 | 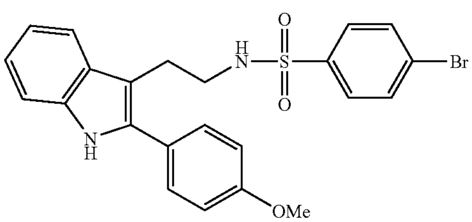 | 3.35 | A | 501 |
| 11 | 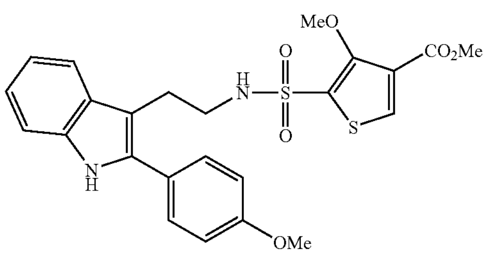 | 3.92 | A | 463 |
| 12 | 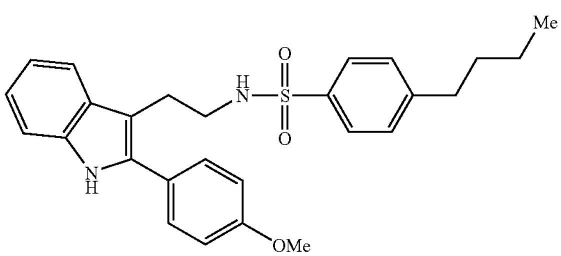 | 3.24 | A | 484 |
| 13 | 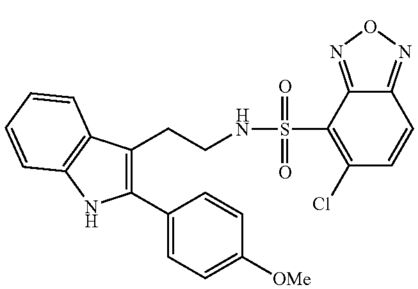 | 3.66 | A | 533 |

-continued

| Ex. # | Structure | RT (min.) | HPLC Method | M/z (MH)+ |
|---|---|---|---|---|
| 14 | 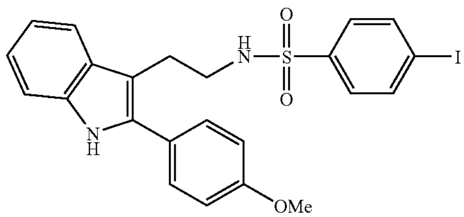 | 2.01 | B | 496 |
| 15 | 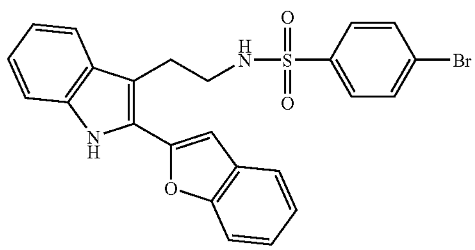 | 3.12 | A | 451 |
| 16 | 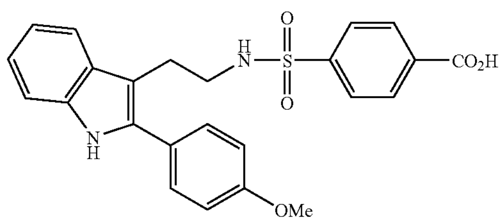 | 4.28 | A | 487 |
| 17 | 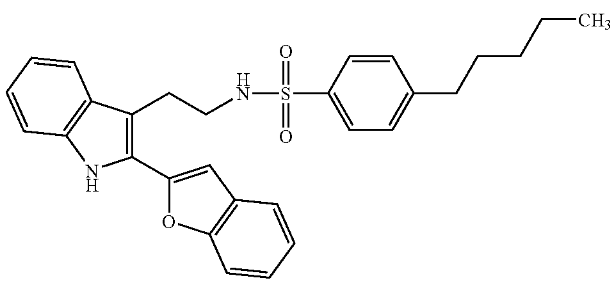 | 3.73 | A | 431 |
| 18 | 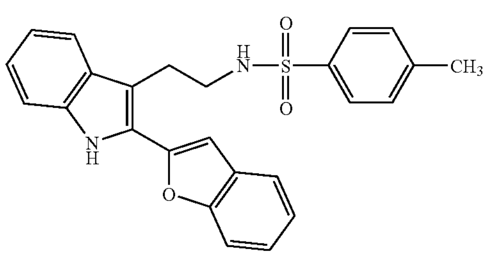 | 1.94 | B | 490 |
| 19 | 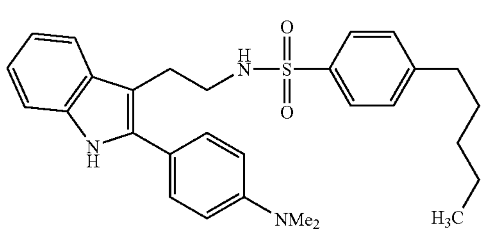 | 4.16 | A | 491 |

-continued

| Ex. # | Structure | RT (min.) | HPLC Method | M/z (MH)+ |
|---|---|---|---|---|
| 20 | 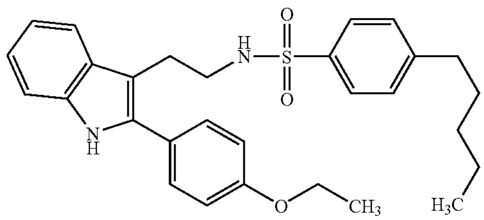 | 4.03 | A | 507 |
| 21 | 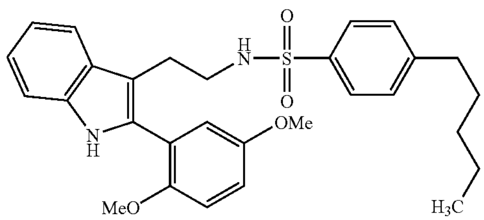 | 4.00 | A | 498 |
| 22 | 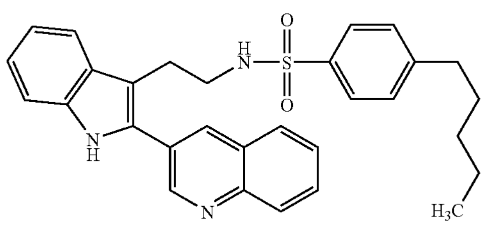 | 4.30 | A | 538 |
| 23 | 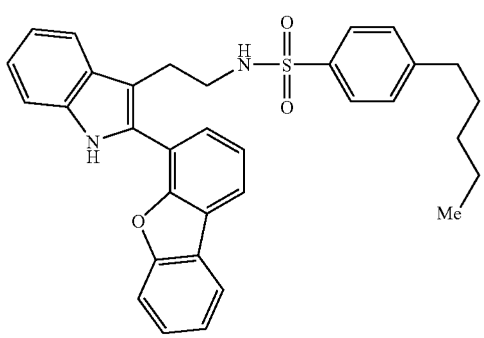 | 4.24 | A | 515 |
| 24 | 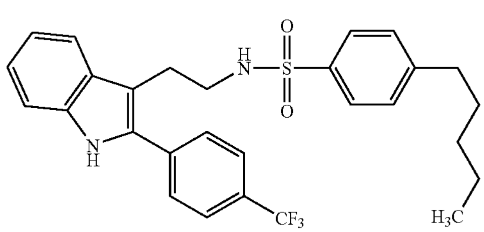 | 4.11 | A | 505 |

-continued

| Ex. # | Structure | RT (min.) | HPLC Method | M/z (MH)+ |
|---|---|---|---|---|
| 25 | 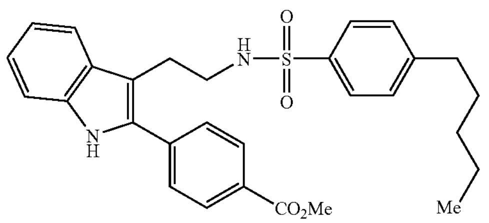 | 3.89 | A | 505 |
| 26 | 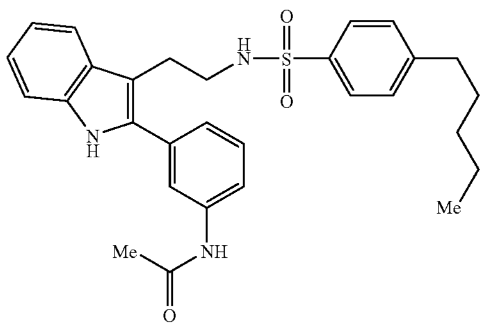 | 1.97 | B | 478 |

Example 27

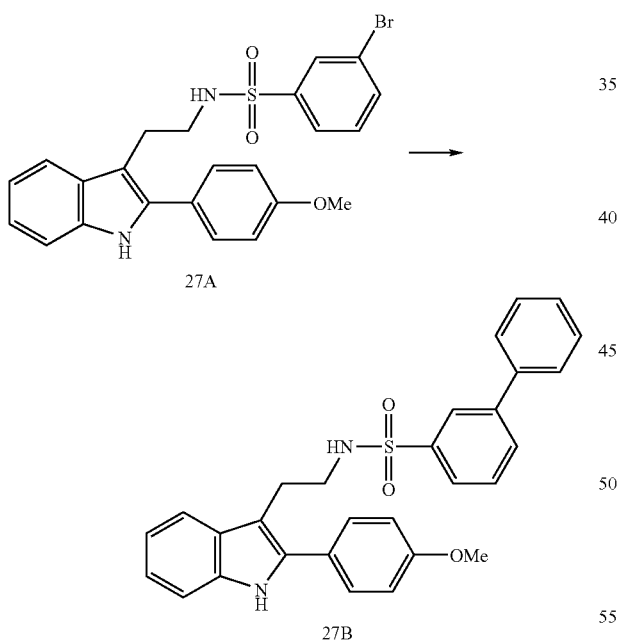

To a solution of the bromide 27A (prepared as described above for the preparation of Examples 1 to 26) (40 mg, 0.082 mmol) in 1,4-dioxane (0.8 mL) was added benzeneboronic acid (13 mg, 0.11 mmol) and 2M aqueous sodium carbonate (0.16 mL), followed by tetrakis triphenyl phosphine palladium (4.6 mg, 0.004 mmol). The mixture was degassed by bubbling through a stream of nitrogen for 5 min, then heated at 80° C. for 3 h. The mixture was then partitioned between ethyl acetate (10 mL) and water (10 mL). The organic layer was washed with saturated aqueous sodium bicarbonate and brine, then dried over sodium sulfate and concentrated. The residue was purified by preparative TLC (silica, 0.5 mm, 10 cm×20 cm, 20% ethyl acetate in hexanes) to provide the title compound 27B as a yellow solid (28 mg, 71% yield). MS (E+) m/z: 484 (MH+); LC retention time (Method A): 3.87 min.

Example 28

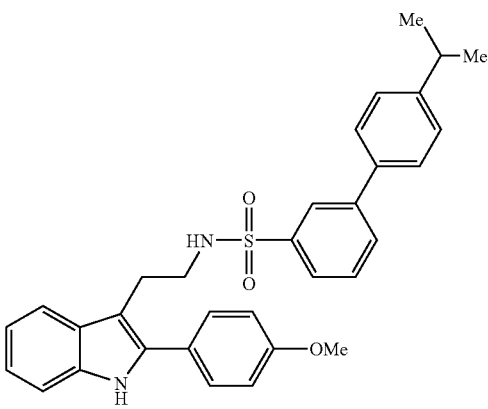

The title compound was prepared from bromide 27A as described above for the preparation of the title compound of Example 27 (27B). MS (E+) m/z: 526 (MH+); LC retention time (Method A): 4.22 min.

Examples 29 to 32

The following Examples 29 to 32 were prepared from the title compound of Example 9 following the procedure described above for the preparation of the title compound of examples 27 and 28 from the bromide 27A.

| Ex. # | Structure | RT (min.) | HPLC Method | M/z (MH)+ |
|---|---|---|---|---|
| 29 | 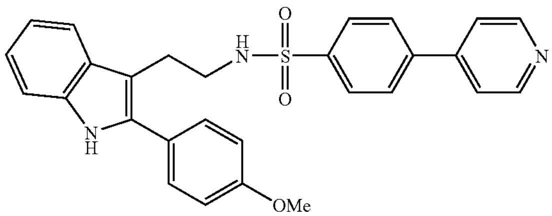 | 2.66 | B | 485 |
| 30 | 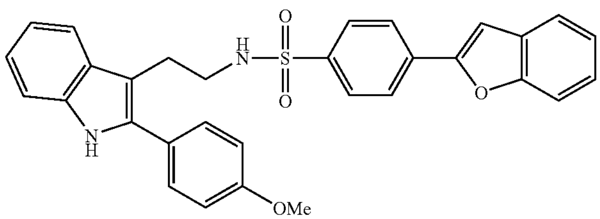 | 4.08 | A | 524 |
| 31 | 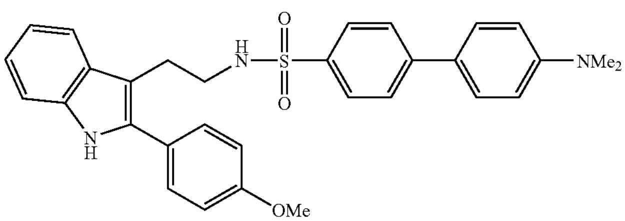 | 3.54 | A | 526 |
| 32 | 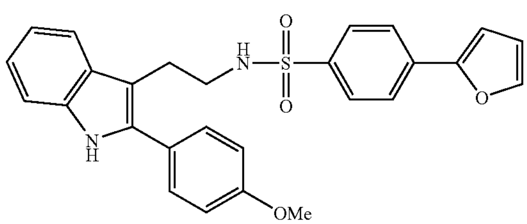 | 3.63 | A | 474 |

Example 33

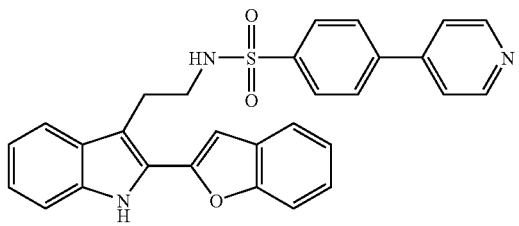

The title compound was prepared from the title compound of Example 14 following the procedure described above for the preparation of the title compound of Example 27 (27B) from the bromide 27A. MS (E+) m/z: 494 (MH+); LC retention time (Method B): 2.97 min.

Example 34

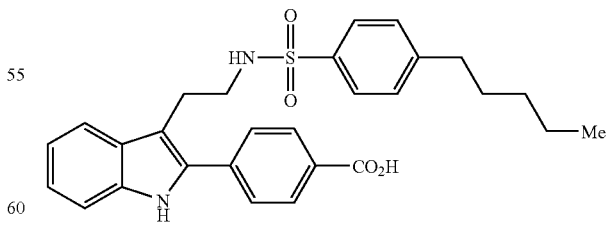

A solution of the title compound of Example 24 (62 mg, 0.12 mmol) in THF (1 mL) was treated with 2N aqueous LiOH (0.2 mL) and allowed to stir at room temperature for 48 h. The reaction mixture was then partitioned between ethyl acetate and 1N HCl. The organic layer was dried over sodium sulfate and concentrated to give the title compound as a solid (60 mg, 98% yield). MS (E+) m/z: 491 (MH+); LC retention time (Method A): 3.92 min.

Example 35

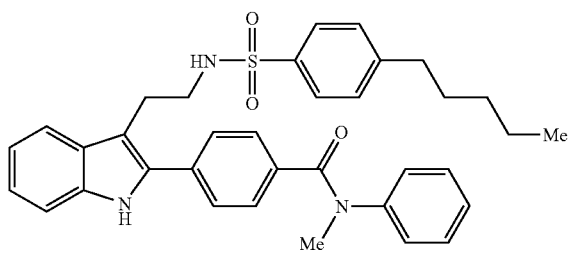

To a solution of the title compound of Example 34 (10 mg, 0.02 mmol) in dichloromethane (0.3 mL) was added EDC (5.75 mg, 0.03 mmol) followed by DMAP (3.6 mg, 0.03 mmol). The solution was allowed to stir 16 h at room temperature. The solvent was then removed by nitrogen stream, and the residue purified by preparative HPLC to give the product as a yellow solid (9 mg, 75% yield) MS (E+) m/z: 580 (MH+); LC retention time (Method A): 4.06 min.

Examples 36 TO 56

The following Examples 36 to 56 were prepared from the title compound 34 following the procedure described above for the preparation of the title of Example 35.

| Ex. # | Structure | RT (min) | HPLC Method | M/z (MH)+ |
|---|---|---|---|---|
| 36 | 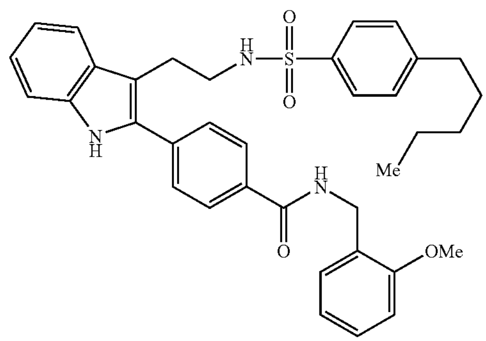 | 4.09 | A | 610 |
| 37 | 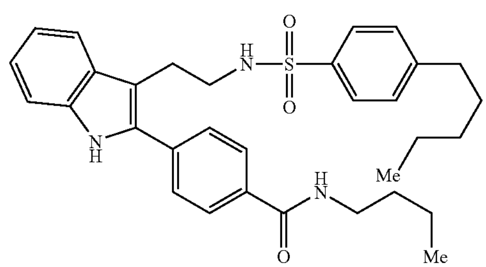 | 4.09 | A | 546 |
| 38 | 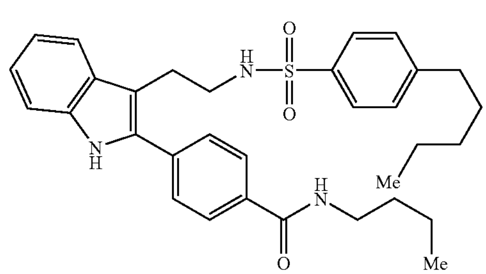 | 3.99 | A | 544 |

-continued

| Ex. # | Structure | RT (min) | HPLC Method | M/z (MH)+ |
|---|---|---|---|---|
| 39 | 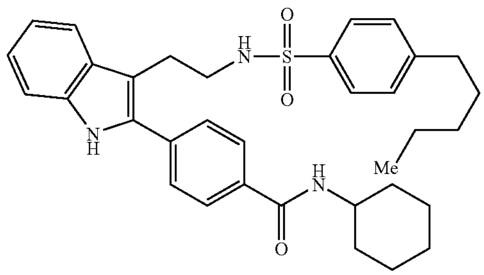 | 4.57 | A | 572 |
| 40 | 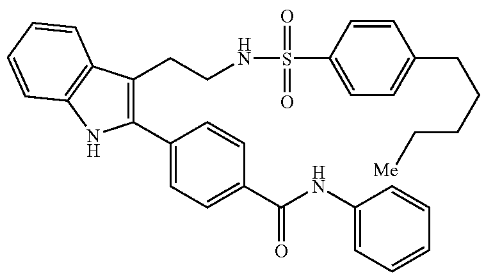 | 4.12 | A | 566 |
| 41 | 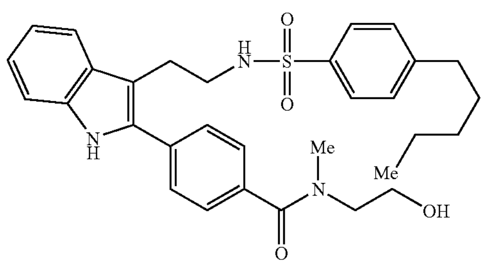 | 3.82 | A | 548 |
| 42 | 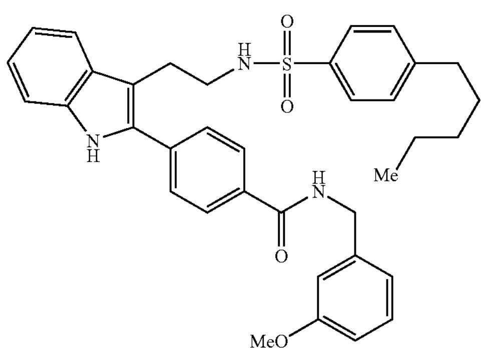 | 4.06 | A | 610 |
| 43 | 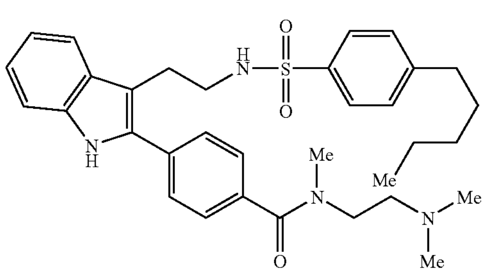 | 3.38 | A | 575 |

-continued
| Ex. # | Structure | RT (min) | HPLC Method | M/z (MH)+ |
|---|---|---|---|---|
| 44 | 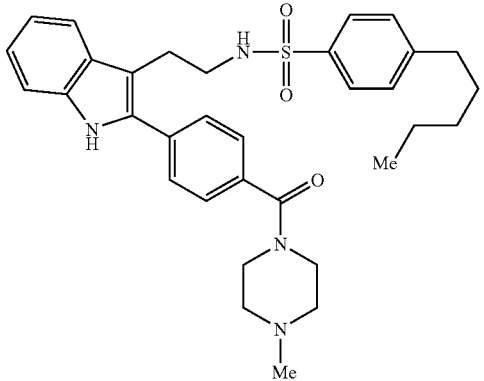 | 3.37 | A | 573 |
| 45 | 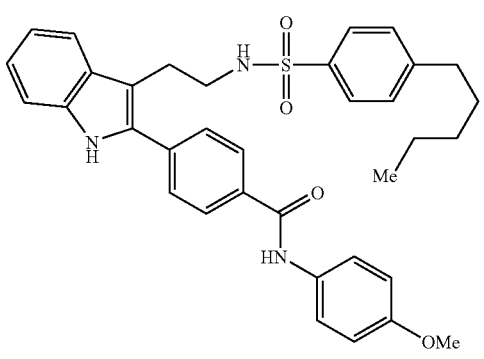 | 4.07 | A | 596 |
| 46 | 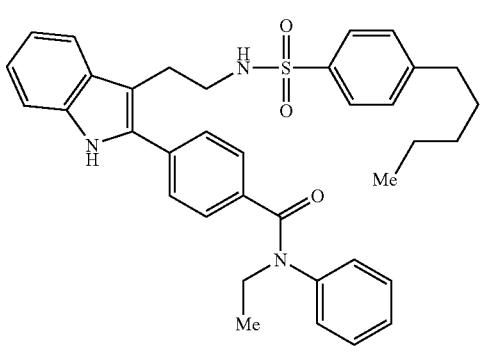 | 4.14 | A | 594 |
| 47 | 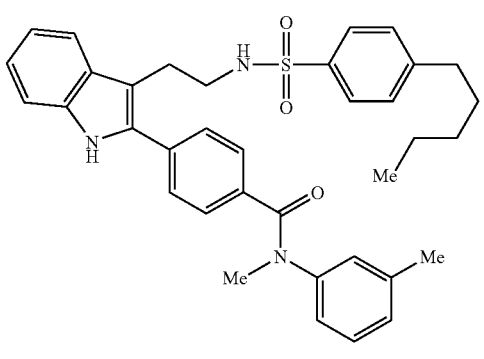 | 4.15 | A | 594 |

-continued

| Ex. # | Structure | RT (min) | HPLC Method | M/z (MH)+ |
|---|---|---|---|---|
| 48 | 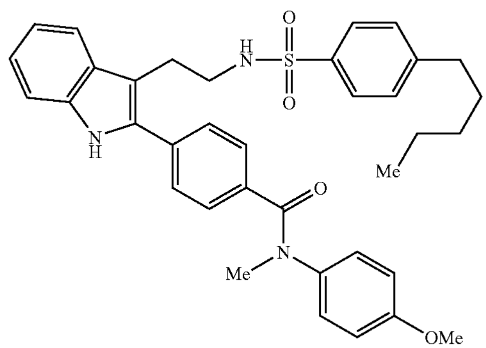 | 4.07 | A | 610 |
| 49 | 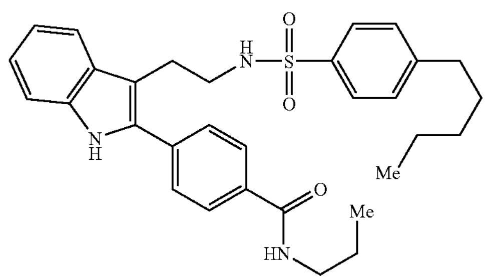 | 3.99 | A | 532 |
| 50 | 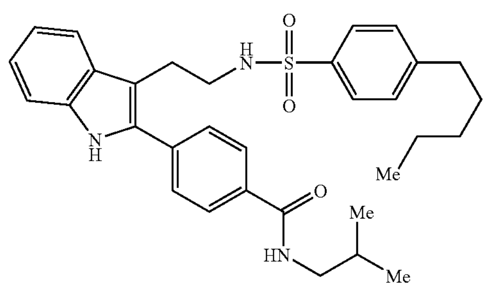 | 4.08 | A | 546 |
| 51 | 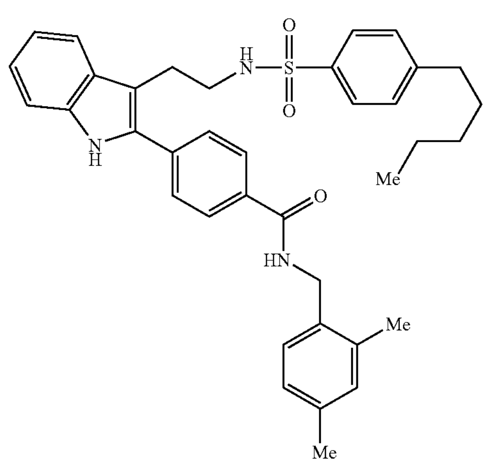 | 4.25 | A | 594 |

| Ex. # | Structure | RT (min) | HPLC Method | M/z (MH)+ |
|---|---|---|---|---|
| 52 | 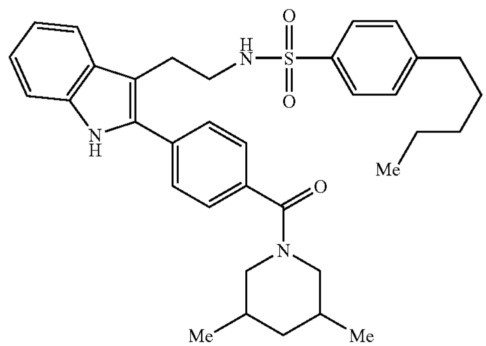 | 4.31 | A | 586 |
| 53 | 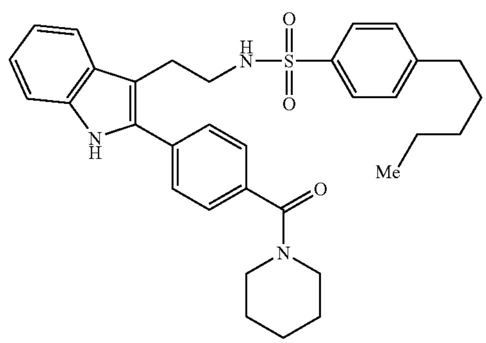 | 4.08 | A | 558 |
| 54 | 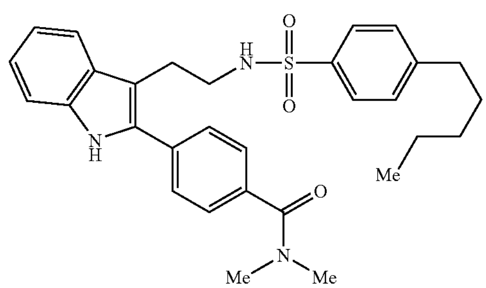 | 3.89 | A | 518 |
| 55 | 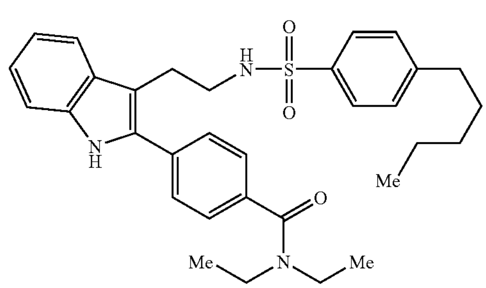 | 4.03 | A | 546 |

-continued

| Ex. # | Structure | RT (min) | HPLC Method | M/z (MH)+ |
|---|---|---|---|---|
| 56 | 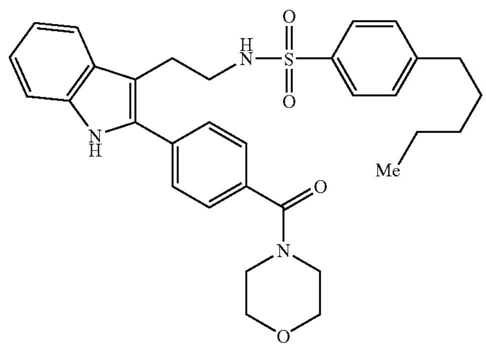 | 3.99 | B | 560 |

Example 57

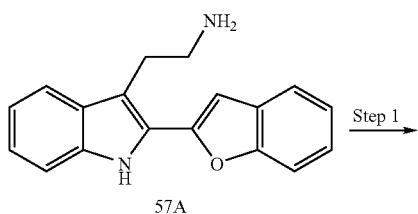

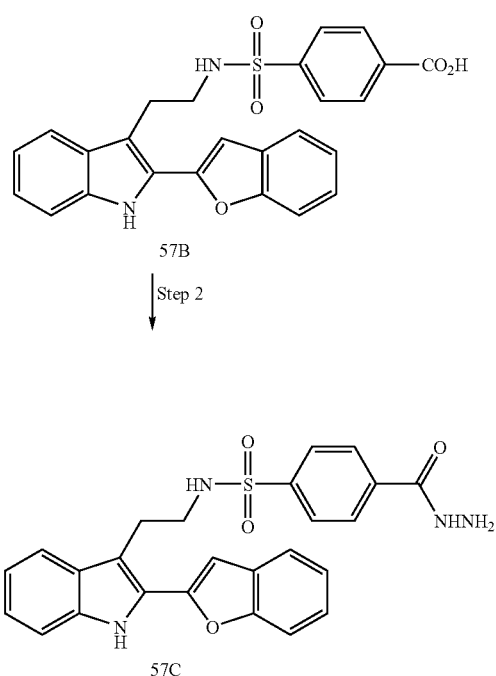

Step 1:

To a solution of the amine 57A [prepared in a manner analogous to the preparation of 1B from 1A)] (136 mg, 0.493 mmol) in dichloromethane (5 mL) at 0° C. was added triethylamine (0.21 mL, 1.48 mmol) followed by 4-chlorosulfonyl benzoic acid (141 mg, 0.64 mmol). The heterogeneous mixture was allowed to warm to room temperature over 30 min, then allowed to stir at room temperature for 3 h. The reaction mixture was then partitioned between ethyl acetate and 1N aqueous HCl. The organic layer was dried over sodium sulfate and concentrated to give the crude product 57B (227 mg) which was used without further purification. MS (E+) m/z: 461 (MH+); LC retention time (Method A): 3.43 min.

Step 2:

To a solution of the acid 57B (126 mg, 0.27 mmol) in THF (3 mL) was added CDI (47 mg, 0.29 mmol), and the resulting solution was allowed to stir at room temperature for 1 h. A solution of hydrazine in THF (1M, 0.54 mL) was then added to the reaction mixture, which was stirred another 35 min at room temperature, then partitioned between ethyl acetate and 1N aqueous HCl. The organic layer was washed with 1N aqueous sodium hydroxide followed by saturated aqueous sodium bicarbonate and brine. The basic aqueous layer was acidified with 1N aqueous HCl and washed with ethyl acetate. The organic layer was dried over sodium sulfate and concentrated to give recovered starting material 57B (68 mg). The initial organic phase (containing title compound 57C) was dried over sodium sulfate and concentrated to give the title compound 57C as a pale yellow oil (58 mg, 99% yield based on recovered starting material). MS (E+) m/z: 475 (MH+); LC retention time (Method A): 3.06 min.

Examples 58 to 65

The following Examples 58 to 65 were prepared from 57B following the same procedure used to describe the preparation of the title compounds of Examples 35 to 56 from the title compound of Example 34.

| Ex. # | Structure | RT (min) | HPLC Method | M/z (MH)+ |
|---|---|---|---|---|
| 58 | 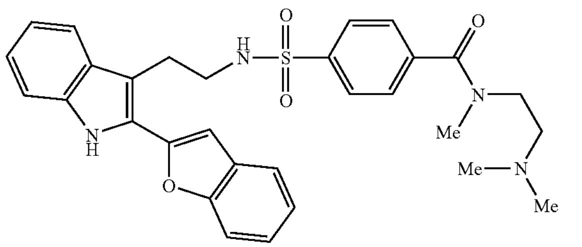 | 2.82 | B | 546 |
| 59 | 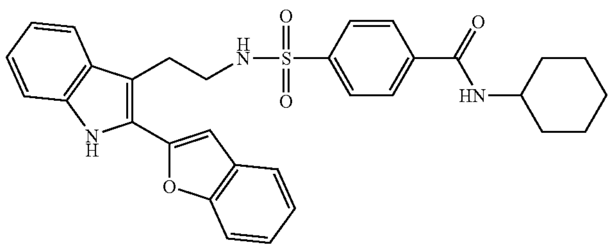 | 3.82 | A | 543 |
| 60 | 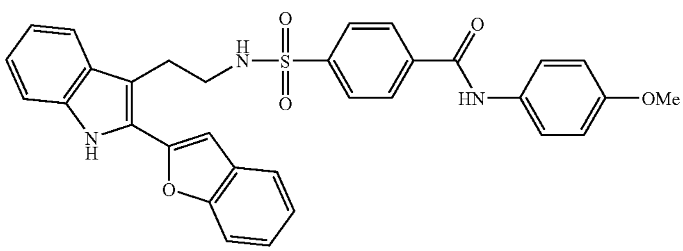 | 3.69 | A | 567 |
| 61 | 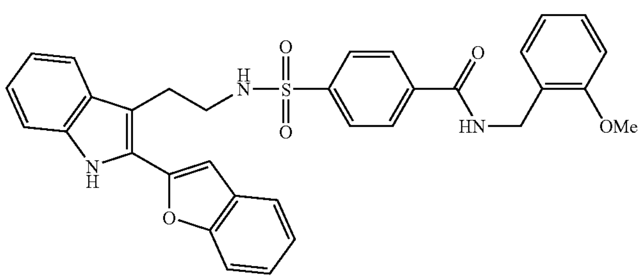 | 3.74 | A | 581 |
| 62 | 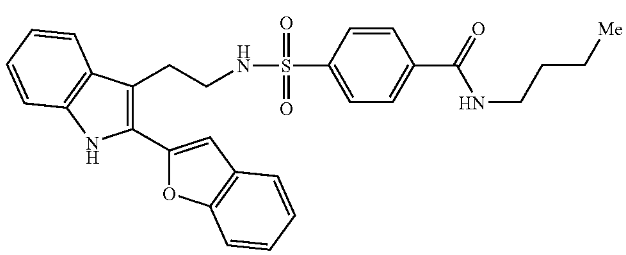 | 3.69 | A | 517 |

| Ex. # | Structure | RT (min) | HPLC Method | M/z (MH)+ |
|---|---|---|---|---|
| 63 | 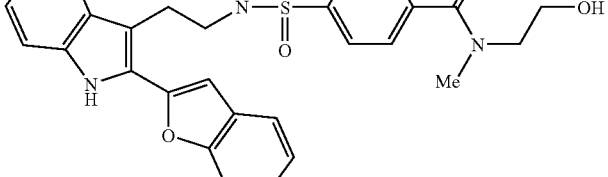 | 3.35 | A | 519 |
| 64 | 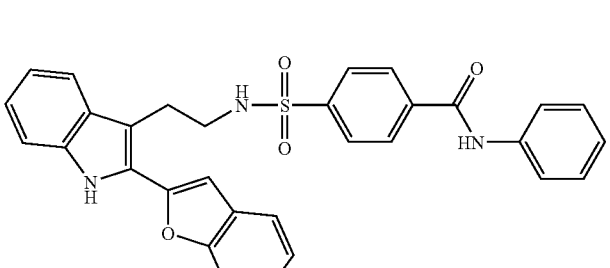 | 3.81 | A | 537 |
| 65 | 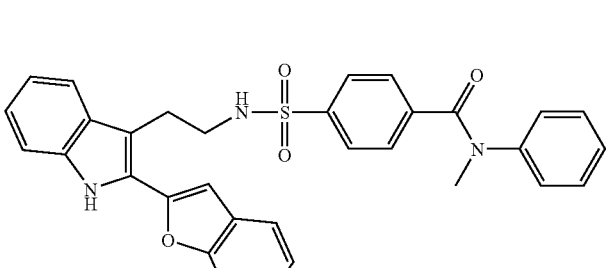 | 3.58 | A | 551 |

Example 66

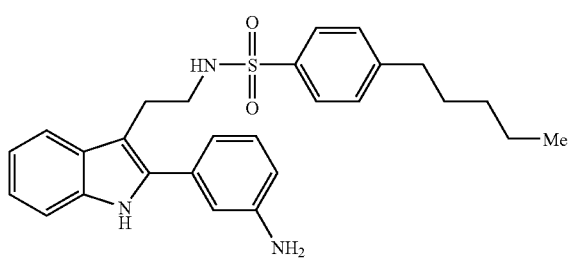

To a solution of the title compound of Example 25 (1.91 g, 3.19 mmol) in ethanol (25 mL) was added a solution of KOH (2 g) in water (25 mL). The mixture was heated in a sealed tube at 130° C. for 35 h. After cooling, the ethanol was removed under reduced pressure, and the residue partitioned between dichloromethane (100 mL) and water (50 mL). the organic layer was dried over sodium sulfate and concentrated to give the product as a yellow oil (1.40 g, 95% yield). MS (E+) m/z: 463 (MH+); LC retention time (Method A): 3.45 min.

Example 67

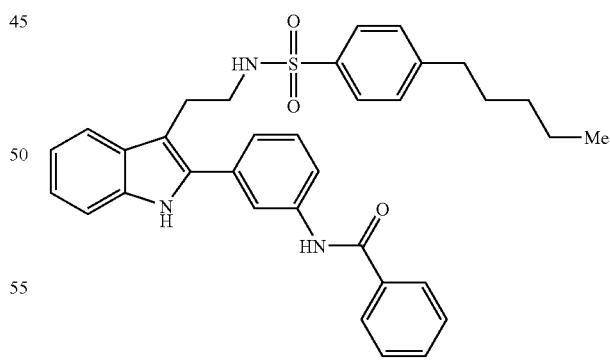

To a solution of the title compound of Example 66 (15 mg, 0.032 mmol) in dichloromethane (0.5 mL) was added Hunig's base (0.017 mL, 0.09 mmol) followed by benzoyl chloride (0.005 mL, 0.04 mmol). The reaction mixture was stirred for 3 h at room temperature, then concentrated and purified by preparative HPLC to give the product as a yellow oil (15 mg, 97% yield). MS (E+) m/z: 567 (MH+); LC retention time (Method A): 4.14 min.

Examples 68 to 75

The following Examples 68 to 75 were prepared from the title compound of Example 66 following the same procedure described for the preparation of the title compounds of Example 67.

| Ex. # | Structure | RT (min) | HPLC Method | M/z (MH)+ |
|---|---|---|---|---|
| 68 | 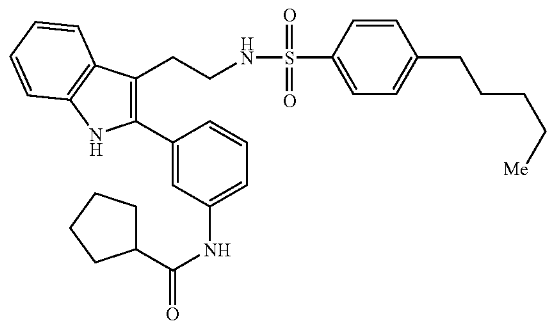 | 4.19 | A | 559 |
| 69 | 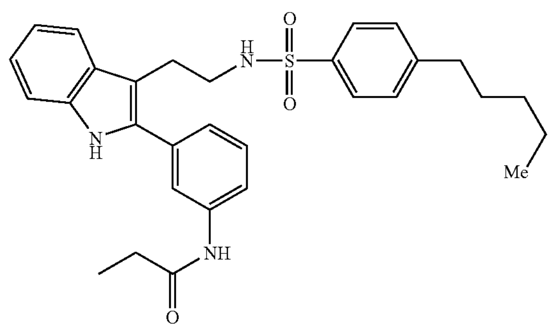 | 3.98 | A | 519 |
| 70 | 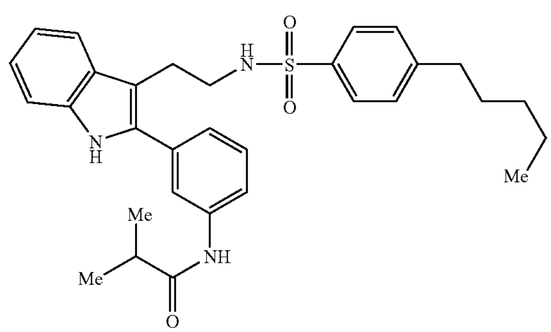 | 4.05 | A | 533 |
| 71 | 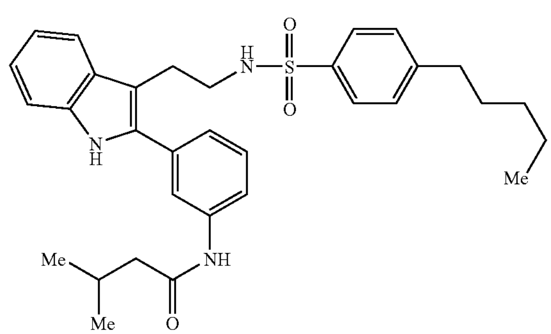 | 4.14 | A | 547 |

-continued

| Ex. # | Structure | RT (min) | HPLC Method | M/z (MH)+ |
|---|---|---|---|---|
| 72 | 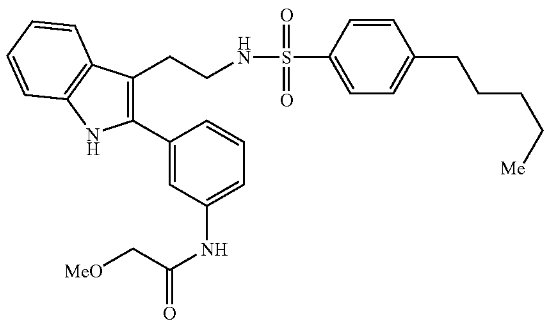 | 4.02 | A | 535 |
| 73 | 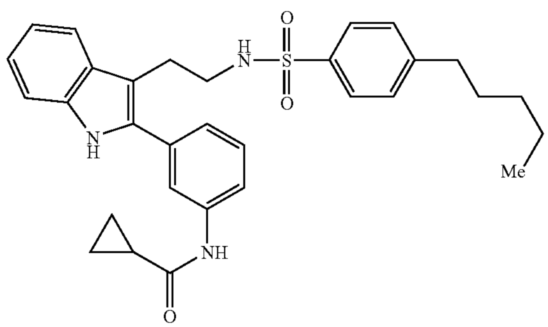 | 4.03 | A | 531 |
| 74 | 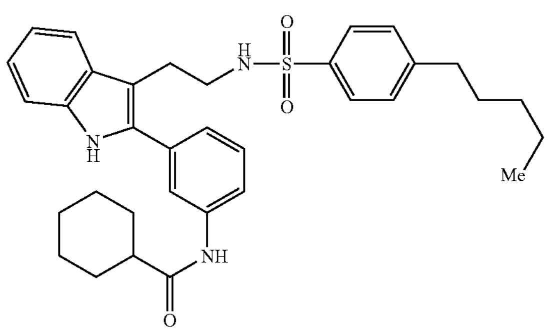 | 4.26 | A | 573 |
| 75 | 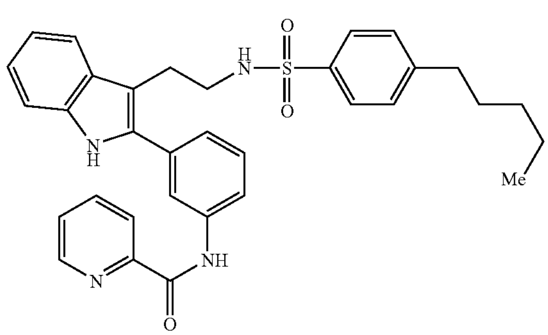 | 3.93 | A | 568 |

Example 76

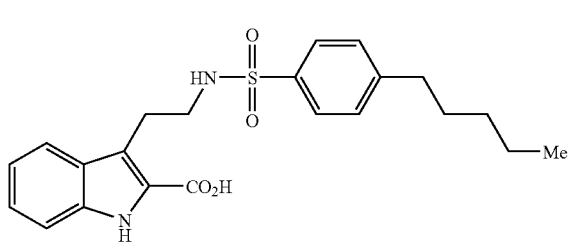

A mixture of tryptamine 2-carboxylic acid [prepared by the method of Soti, et al. *Synth. Comm.* 1993, 23(12) 1689], sodium carbonate (3.1 g, 29.2 mmol), and 4-pentylbenzene-1-sulfonyl chloride (3.22 g, 13.0 mmol) was heated at 80° C. for 55 min. The reaction mixture was then cooled and partitioned between ethyl acetate and 1N HCl. The organic layer was filtered over celite to remove the suspended solid. The filtrate was dried over sodium sulfate and concentrate to give 3.25 g of a crude brown oil which solidified upon standing. The crude material was adsorbed on silica and purified by flash column chromatography (silica, 10% MeOH/5% ethyl acetate/5% hexanes/80% dichloromethane) to give the product (1.76 h, 36% yield) as an amorphous solid. MS (E+) m/z: 415 (MH+); LC retention time (Method A): 3.75 min.

Example 77

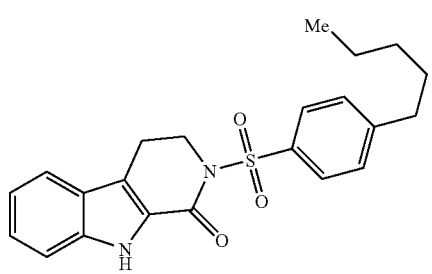

To the title compound of Example 76 (58 mg, 0.14 mmol) in DMF (0.5 mL) was added 1,1-carbonyldiimidazole (CDI) (25 mg, 0.15 mmol). After 3 h at room temperature, another portion of CDI (25 mg, 0.15 mmol) was added, and the mixture was heated at 115° C. for 6 h. The reaction mixture was then partitioned between ethyl acetate and water, and the organic layer washed with brine, dried over sodium sulfate, and concentrated. The resulting oil was purified by flash column chromatography (silica, 25% ethyl acetate in hexanes) to give the title compound (32 mg, 58% yield) as a white solid. MS (E+) m/z: 397 (MH+); LC retention time (Method A): 3.99 min.

Example 78

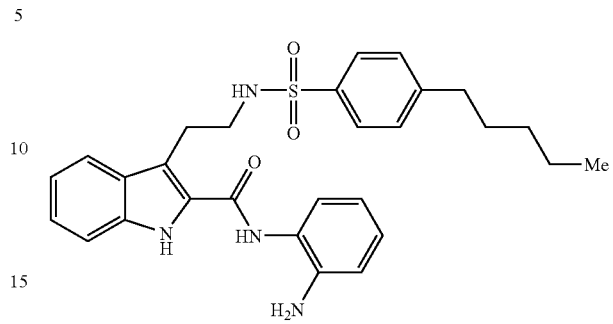

A solution of the title compound of Example 76 (71 mg, 0.17 mmol) in DMF (1 mL) at room temperature was treated sequentially with HOBt monohydrate (24 mg, 0.18 mmol), o-phenylenediamine (18.4 mg, 0.17 mmol) and EDC (34 mg, 0.18 mmol). The mixture was allowed to stir 30 min at room temperature, then partitioned between ethyl acetate and water. The organic layer was washed with saturated aqueous sodium bicarbonate, then brine, dried over sodium sulfate, and concentrated to give the title compound (75 mg, 88% yield) as a pale yellow oil. MS (E+) m/z: 505 (MH+); LC retention time (Method A): 3.63 min.

Example 79

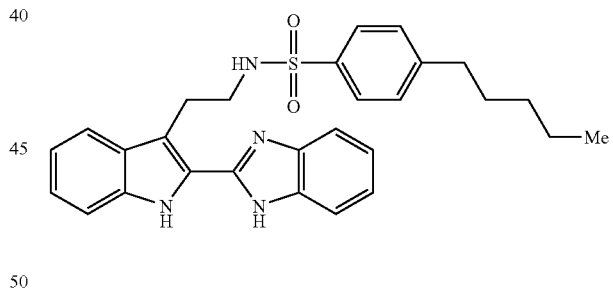

A mixture of tryptamine 2-carboxylic acid [prepared by the method of Soti, et al. *Synth. Comm.* 1993, 23(12) 1689], sodium carbonate (3.1 g, 29.2 mmol), and 4-pentylbenzene-1-sulfonyl chloride (3.22 g, 13.0 mmol) was heated at 80° C. for 55 min. The reaction mixture was then cooled and partitioned between ethyl acetate and 1N HCl. The organic layer was filtered over celite to remove the suspended solid. The filtrate was dried over sodium sulfate and concentrate to give 3.25 g of a crude brown oil which solidified upon standing. The crude material was adsorbed on silica and purified by flash column chromatography (silica, 10% MeOH/5% ethyl acetate/5% hexanes/80% dichloromethane) to give the product (1.76 h, 36% yield) as an amorphous solid. MS (E+) m/z: 487 (MH+); LC retention time (Method A): 3.49 min.

Example 80

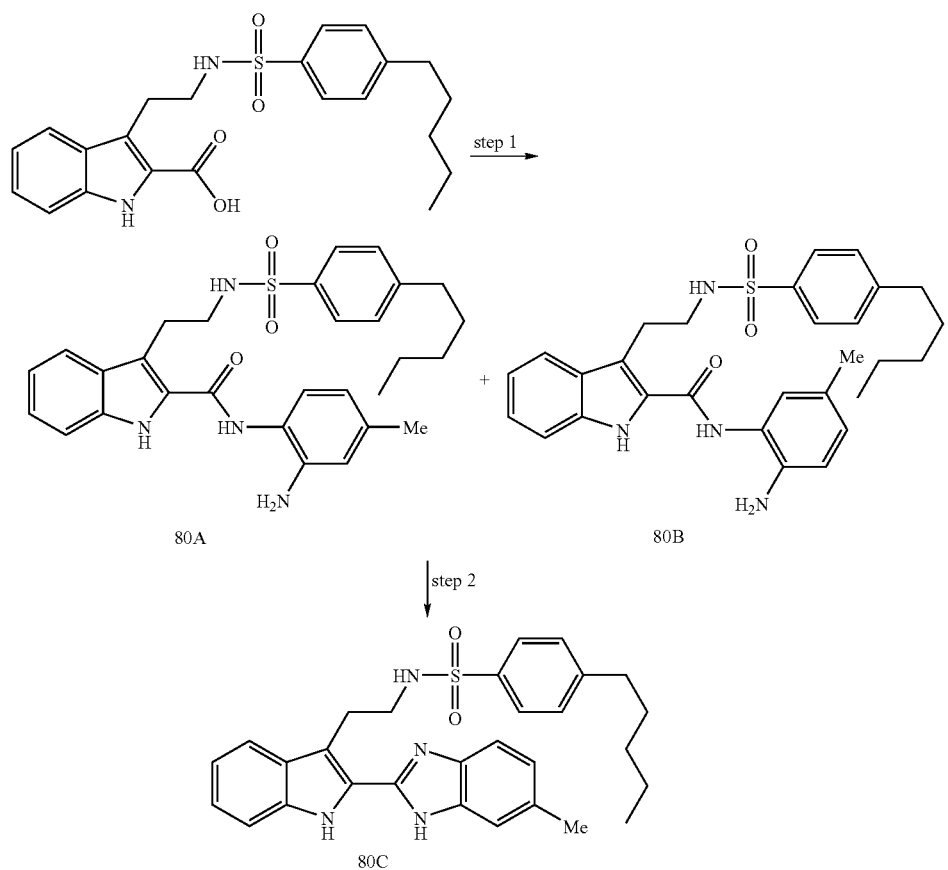

Step 1:

The mixture of amides 80A and 80B was prepared from the title compound of Example 76 following the procedure described above for the preparation of the title compound of Example 78, replacing o-phenylene diamine with 3,4-diamino toluene. MS (E+) m/z: 519 (MH$^+$); LC retention time (Method A): 3.79 min.

Step 2:

The title compound 80C was prepared from the mixture of amides 80A and 80B following the procedure described above for the preparation of the title compound of Example 79. MS (E+) m/z: 501 (MH$^+$); LC retention time (Method A): 3.48 min.

Example 81

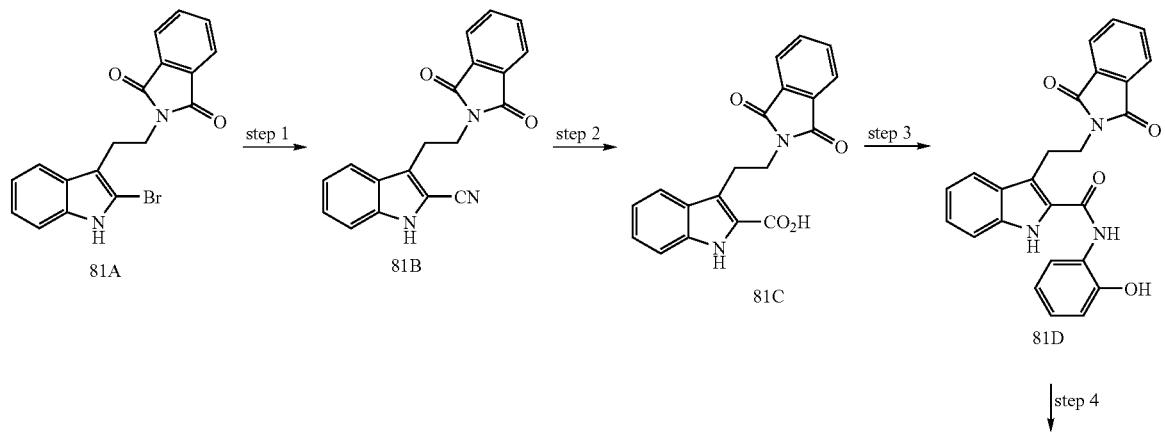

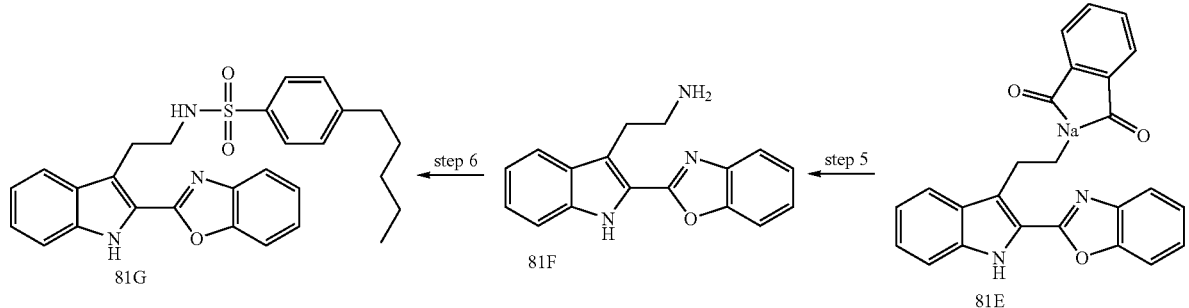

Step 1:
A solution of the bromide 81A [prepared according to the literature report: Chu, L. et al., *Tetrahetron Lett.*, 38(22) 3871-3874 (1997)] (1.99 g, 5.39 mmol) in N-methyl pyrollidinone(NMP) (9 mL) was treated with copper (I) cyanide (869 mg, 9.7 mmol) and heated in a sealed reaction vessel at 150° C. for 22 h. The mixture was poured into water (75 mL) and ethyl acetate (75 mL) was added. The mixture was stirred rapidly for 10 min. The organic layer was then separated, concentrated, and the residue purified by flash column chromatography (silica, 25% ethyl acetate in hexanes, then 30% ethyl acetate in hexanes) to give the product 81B (662 mg, 39% yield) as a solid. LC retention time (Method A): 3.12 min.

Step 2:
A mixture of the product of Step 1 (81B) (45 mg, 0.14 mmol) and sodium peroxide (66 mg, 0.84 mmol) in water (4 mL) was heated at 60° C. for 2 h. The reaction mixture was then partitioned between 1N HCl (10 mL) and ethyl acetate (10 mL). The organic layer was dried over sodium sulfate and concentrated to give the intermediate compound (81C) which was used in the next step with no further purification. MS (E+) m/z: 335 (MH$^+$); LC retention time (Method A): 2.25 min.

Step 3:
To a solution of the product of Step 2 (81C) (0.14 mmol) in DMF (2 mL) was added 1,1-carbonyl diimidazole (CDI) (24 mg, 0.15 mmol) and the resulting solution heated at 40° C. for 1 h. 2-Aminophenol (15.3 mg, 0.14 mmol) was then added, and the resulting solution stirred 16 h at room temperature. The reaction mixture was then partitioned between ethyl acetate (10 mL) and water (10 mL). The organic layer was washed with saturated aqueous sodium bicarbonate and brine, dried over sodium sulfate, and concentrated. The product thus obtained (81D) was used directly in the next step without further purification. LC retention time (Method A): 2.88 min.

Step 4:
A solution of the product of Step 3 (81D) (0.14 mmol) in xylenes (1.5 mL) was treated with p-toluene sulfonic acid (67 mg, 0.35 mmol) and heated at 160° C. for 18 h. The reaction mixture was then partitioned between ethyl acetate (10 mL) and water (10 mL). The organic layer was washed with saturated aqueous sodium bicarbonate and brine, dried over sodium sulfate, and concentrated. The residue was purified by preparative TLC (0.5 mm silica, 20 cm×20 cm, 40% ethyl acetate in hexanes) to give the product 81E (5 mg, 9% yield over 3 steps). MS (E+) m/z: 408 (MH$^+$); LC retention time (Method A): 3.76 min.

Step 5:
To a solution of the product of Step 4 (81E, 5 mg, 0.012 mmol) in methanol (0.4 mL) and THF (0.12 mL) was added hydrazine monohydrate (0.003 mL, 0.048 mmol). The mixture was heated for 2 h at 75° C., then concentrated in vacuo. The residue was purified by preparative TLC (silica, 0.5 mm, 10 cm×10 cm, 1% concentrated ammonium hydroxide, 10% MeOH, 89% dichloromethane) to give the product 81F (2.5 mg, 75% yield). MS (E+) m/z: 278 (MH$^+$); LC retention time (Method A): 2.32 min.

Step 6:
The title compound 81G was prepared following the same procedure described above for the preparation of the title compound of Example 1C from 1B. MS (E+) m/z: 488 (MH$^+$); LC retention time (Method A): 4.25 min.

Example 82

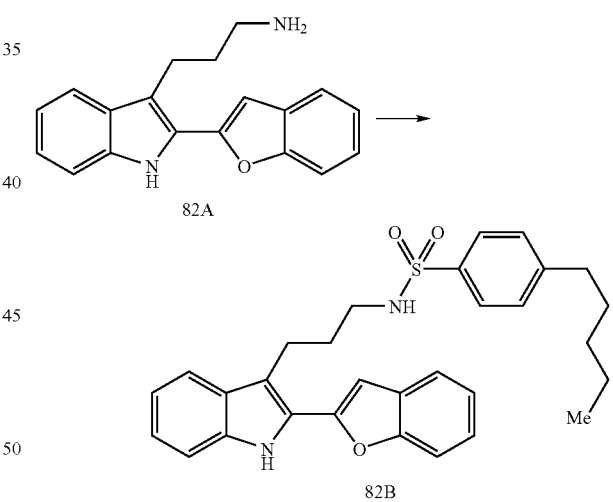

The amine 82A was prepared from homotryptamine (Takechi, H.; Machida, M.; Kanaoka, Y. *Chem. Pharm. Bull.* 1988, 36, 2853) following procedures analogous to those described above for the preparation of amine 1B. The title compound 82B was prepared from 82A following the procedure described for the preparation of the title compound of Example 1 (1C). (E+) m/z: 501 (MH$^+$); LC retention time (Method A): 4.83 min.

Examples 83 to 85

The following Examples 83 to 85 were prepared from 82A in following the procedure described for the preparation of the title compound of Example 82.

| Ex. # | Structure | RT (min) | HPLC Method | M/z (MH)+ |
|---|---|---|---|---|
| 83 | 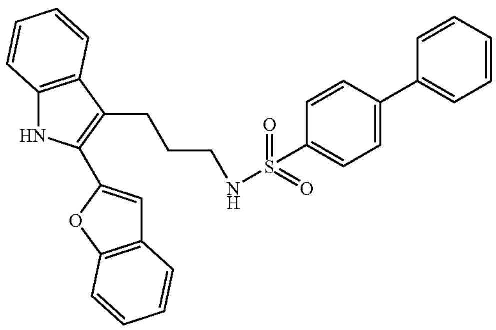 | 4.55 | A | 507 |
| 84 | 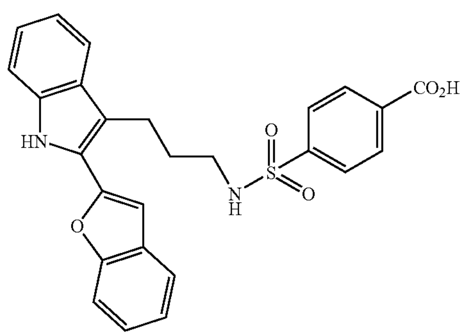 | 4.06 | A | 475 |
| 85 | 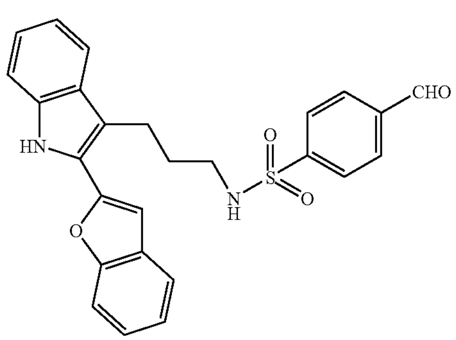 | 3.73 | A | 459 |

Example 86

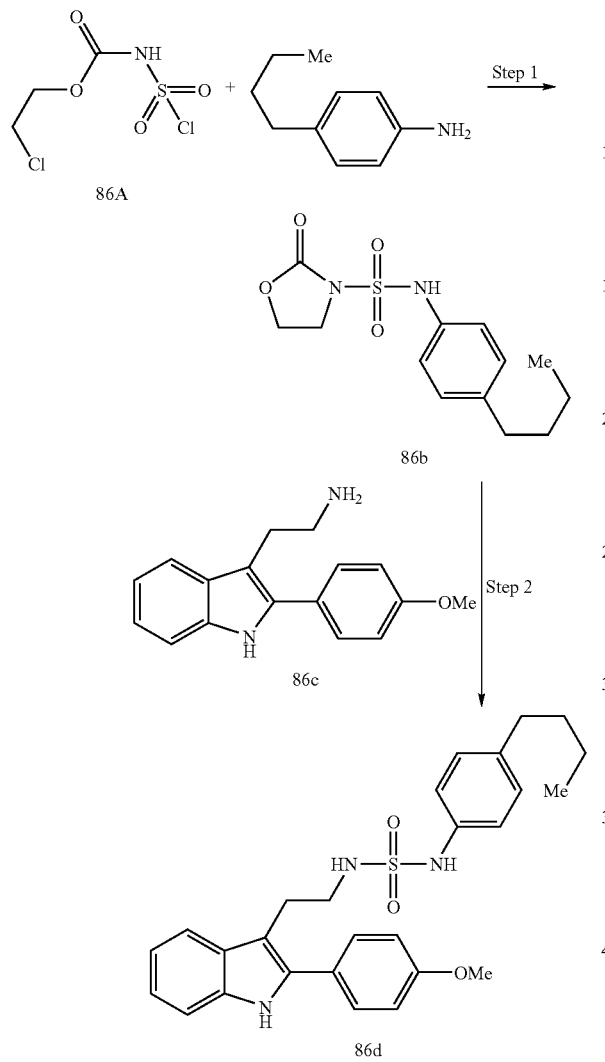

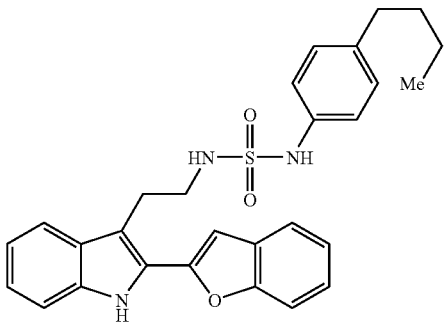

Step 1:

To a stirred solution of chlorosulfonyl associate (0.03 mL, 0.31 mmol) in dichloromethane (1.5 mL) cooled to 0° C. was added 2-chloroethanol (0.021 mL, 0.31 mmol) at such a rate that the reaction temperature did not exceed 5° C. After stirring at 0° C. for 1.5 h, a solution of 4-butyl aniline (0.048 mL, 0.31 mmol) and triethyl amine (0.03 mL) in dichloromethane (3 mL) was added slowly so that the reaction temperature remained under 5° C. When the addition was complete, the solution was allowed to warm to room temperature, and stirred for 12 h. The reaction was then quenched with 1N aqueous HCl. The organic phase was separated and the aqueous phase washed with dichloromethane (2×10 mL). The combined organic extracts were dried over sodium sulfate and concentrated. (E+) m/z: 299 (MH+); LC retention time (Method B): 2.89 min.

Step 2:

To a stirred solution of the product of step 1 (0.075 mmol) in acetonitrile (1.25 mL) was added triethylamine (0.07 mL) and the amine 86c (prepared in a manner analogous to the preparation of amine 1b, 20 mg, 0.075 mmol). The solution was heated at 90° C. for 3 h, then evaporated, and the crude material purified by preparative HPLC to give the title compound 86d as a solid (16 mg). (E+) m/z: 478 (MH+); LC retention time (Method B): 2.15 min.

Example 87

The title compound was prepared following the procedures described above for the preparation of the title compound of Example 86. (E+) m/z: 488 (MH+); LC retention time (Method B): 2.26 min.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound according to Formula I:

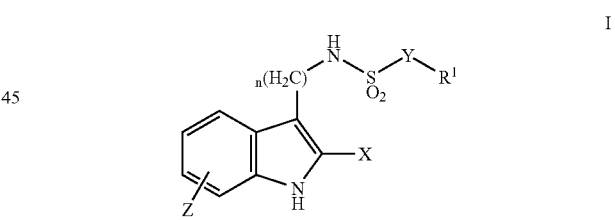

including enantiomers, diastereomers, salts and solvates thereof, wherein:

Z is hydrogen;

X is selected from the group consisting of —C(O)NR$^2$R$^3$, —C(O)OH, aryl, heteroaryl and —C(O)—, wherein the —C(O)— is bonded to the nitrogen of the sulfonylamino group to form a six- or seven-membered lactam, wherein each aryl and heteroaryl may optionally be substituted with one or more substituents selected from the group consisting of halo, alkyl, perfluoroalkyl, alkoxy, amino, carboxylic acid, ester and amide;

Y is selected from the group consisting of a direct bond, aryl, heteroaryl and NR$^2$;

R$^1$ is selected from the group consisting of H, alkyl, cycloalkyl, aryl, heteroaryl, amido, amino, hydroxyl, alkoxy, halo,

carboxylic acid, alkylester and

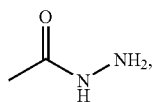

wherein each alkyl, aryl, heteroaryl, amido and amino may optionally be substituted with one or more substituents selected from the group consisting of alkyl, cycloalkyl, aryl, heteroaryl, amido, amino, hydroxyl, alkoxy and halo;

$R^2$ and $R^3$ are independently selected from the group consisting of H, alkyl, cycloalkyl, heterocyclyl, aryl and heteroaryl; and n is 2 or 3.

2. A compound according to claim 1, wherein X is selected from the group consisting of aryl and heteroaryl.

3. A compound according to claim 2, wherein
Y is a direct bond; and
$R^1$ is selected from the group consisting of aryl and heteroaryl.

4. A pharmaceutical composition, comprising a compound according to claim 1 and a pharmaceutically acceptable carrier therefor.

* * * * *

UNITED STATES PATENT AND TRADEMARK OFFICE
CERTIFICATE OF CORRECTION

| | | |
|---|---|---|
| PATENT NO. | : 7,429,611 B2 | Page 1 of 1 |
| APPLICATION NO. | : 11/232063 | |
| DATED | : September 30, 2008 | |
| INVENTOR(S) | : Weinstein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 245 days.

Signed and Sealed this

Fifth Day of October, 2010

David J. Kappos
*Director of the United States Patent and Trademark Office*